US008841276B2

(12) United States Patent
Arbiser

(10) Patent No.: US 8,841,276 B2
(45) Date of Patent: Sep. 23, 2014

(54) FULVENE AND FULVALENE ANALOGS AND THEIR USE IN TREATING CANCERS

(71) Applicants: Emory University, Atlanta, GA (US); The United States of America Department of Veterans Affairs, Washington, DC (US)

(72) Inventor: Jack L. Arbiser, Atlanta, GA (US)

(73) Assignees: Emory University, Atlanta, GA (US); The United States of America as represented by the Department of Veterans Affairs, Washington, DC (US)

(*) Notice: Subject to any disclaimer, the term of this patent is extended or adjusted under 35 U.S.C. 154(b) by 0 days.

(21) Appl. No.: 13/970,639

(22) Filed: Aug. 20, 2013

(65) Prior Publication Data
US 2013/0338208 A1  Dec. 19, 2013

Related U.S. Application Data

(63) Continuation of application No. 12/114,601, filed on May 2, 2008, now abandoned.

(60) Provisional application No. 60/927,416, filed on May 3, 2007, provisional application No. 60/934,381, filed on Jun. 13, 2007, provisional application No. 61/047,717, filed on Apr. 24, 2008.

(51) Int. Cl.
| | | |
|---|---|---|
| A01N 43/04 | (2006.01) |
| A61K 31/70 | (2006.01) |
| C09B 7/02 | (2006.01) |
| C07D 407/04 | (2006.01) |
| C07D 233/58 | (2006.01) |
| C07C 13/58 | (2006.01) |
| C07D 471/10 | (2006.01) |
| A61K 31/573 | (2006.01) |
| C07C 35/32 | (2006.01) |
| C07D 307/58 | (2006.01) |
| C07C 39/23 | (2006.01) |
| C07D 295/03 | (2006.01) |
| C07C 275/64 | (2006.01) |
| C07D 209/14 | (2006.01) |
| C07C 211/50 | (2006.01) |
| C07C 13/40 | (2006.01) |
| C07C 13/28 | (2006.01) |
| C07C 233/44 | (2006.01) |
| C07D 233/68 | (2006.01) |
| A61K 31/045 | (2006.01) |
| C07D 311/60 | (2006.01) |
| A61K 31/341 | (2006.01) |
| C07D 209/86 | (2006.01) |
| C07C 237/26 | (2006.01) |
| C07D 261/08 | (2006.01) |
| C07C 69/608 | (2006.01) |
| A61K 31/444 | (2006.01) |
| C07C 25/18 | (2006.01) |
| A61K 31/403 | (2006.01) |
| C07C 251/28 | (2006.01) |
| C07D 309/38 | (2006.01) |
| A61K 31/4164 | (2006.01) |
| C07D 311/82 | (2006.01) |
| A61K 31/015 | (2006.01) |
| A61K 31/5375 | (2006.01) |
| C07D 209/82 | (2006.01) |
| C07C 215/46 | (2006.01) |
| C07D 213/53 | (2006.01) |
| C07C 13/66 | (2006.01) |
| C07C 43/215 | (2006.01) |
| C07D 295/135 | (2006.01) |
| C07C 13/465 | (2006.01) |
| C07D 277/40 | (2006.01) |
| A61K 31/167 | (2006.01) |
| C07C 43/23 | (2006.01) |
| C07D 473/34 | (2006.01) |
| A61K 31/357 | (2006.01) |
| C07D 311/58 | (2006.01) |

(52) U.S. Cl.
CPC ............ *C07D 209/14* (2013.01); *C07D 407/04* (2013.01); *C07C 2103/46* (2013.01); *C07C 2102/08* (2013.01); *C07C 2103/40* (2013.01); *C07D 233/58* (2013.01); *C07C 13/58* (2013.01); *C07D 471/10* (2013.01); *A61K 31/573* (2013.01); *C07C 35/32* (2013.01); *C07C 2103/24* (2013.01); *C07D 307/58* (2013.01); *C07C 39/23* (2013.01); *C07C 2102/42* (2013.01); *C07D 295/03* (2013.01); *C07C 275/64* (2013.01); *C07C 211/50* (2013.01); *C07C 13/40* (2013.01); *C07C 13/28* (2013.01); *C07C 233/44* (2013.01); *C07D 233/68* (2013.01); *A61K 31/045* (2013.01); *C07D 311/60* (2013.01); *A61K 31/341* (2013.01); *C07D 209/86* (2013.01); *C07C 237/26* (2013.01); *C07D 261/08* (2013.01); *C07C 69/608* (2013.01); *A61K 31/444* (2013.01); *C07C 25/18* (2013.01); *A61K 31/403* (2013.01); *C07C 2101/10* (2013.01); *C07C 251/28* (2013.01); *C07D 309/38* (2013.01); *A61K 31/4164* (2013.01); *C07D 311/82* (2013.01); *A61K 31/015* (2013.01); *A61K 31/5375* (2013.01); *C07D 209/82* (2013.01); *C07C 215/46* (2013.01); *C07D 213/53* (2013.01); *C07C 13/66* (2013.01); *C07C 43/215* (2013.01); *C07D 295/135* (2013.01); *C07C 13/465* (2013.01); *C07D 277/40* (2013.01); *A61K 31/167* (2013.01); *C07C 43/23* (2013.01); *C07D 473/34* (2013.01); *A61K 31/357* (2013.01); *C07D 311/58* (2013.01)
USPC ............................................. 514/46; 548/457

(58) Field of Classification Search
None
See application file for complete search history.

*Primary Examiner* — Anna Pagonakis
(74) *Attorney, Agent, or Firm* — Emory Patent Group

(57) ABSTRACT

Compounds, pharmaceutical compositions including the compounds, and methods of preparation and use thereof are disclosed. The compounds are fulvene and/or fulvalene analogs. The compounds and compositions can be used to treat and/or prevent a wide variety of cancers, including drug resistant cancers, as well as numerous inflammatory, degenerative and vascular diseases, including various ocular diseases. Representative fulvene and/or fulvalene analogs include fulvene and fulvalene analogs of various dyes, hormones, sugars, peptides, oligonucleotides, amino acids, nucleotides, nucleosides, and polyols. The compounds are believed to function, at least, by inhibiting Nox or ROS. In some embodiments, the Nox is one that is selectively expressed in cancer cells over normal cells, or one that is expressed in higher amounts in cancer cells over normal cells. Thus, the compounds are novel therapeutic agents for a variety of cancers and other diseases.

3 Claims, 4 Drawing Sheets

FULVENE AND FULVALENE ANALOGS AND THEIR USE IN TREATING CANCERS

CROSS REFERENCE TO RELATED APPLICATIONS

This application is a continuation of U.S. application Ser. No. 12/114,601 filed May 2, 2008, which is a 371 U.S.C. national phase filing of International Patent Application NO. PCT/US2008/062497, which claim the benefit of priority to U.S. Provisional Patent Application Nos. 60/927,416 filed on May 3, 2007; 60/934,381 filed on Jun. 13, 2007, and 61/047,717 filed on Apr. 24, 2008, hereby incorporated by this reference in their entireties.

ACKNOWLEDGEMENTS

This invention was made with government support under Grant No. AR47901 awarded by National Institutes of Health. The government has certain rights in the invention.

FIELD OF THE INVENTION

The present invention relates to novel methods and compositions for the treatment of primary and metastatic cancers. These methods and compositions use fulvenes and/or fulvalenes. These compounds, and pharmaceutical compositions including the compounds, are particularly useful for treating primary and metastatic cancers in humans. The invention also encompasses the varying modes of administration of the therapeutic compounds or compositions.

BACKGROUND OF THE INVENTION

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Cancer is a multistep process, beginning with minor preneoplastic changes, which may under certain conditions progress to neoplasia. Malignant endothelial tumors arise in the setting of autocrine loops involving vascular endothelial growth factor (VEGF) and its major mitogenic receptor vascular endothelial growth factor receptor 2.

Reactive oxygen species (ROS) are believed to be mediators of growth and angiogenesis in cancer. Increased ROS often correlates with cell growth, e.g., Ras-transformed cells and cells treated with growth factors. While non-transformed cells respond to growth factors/cytokines with the regulated production of ROS, tumor cells in culture frequently overproduce $H_2O_2$.

NAD(P)H oxidase (Nox) is a cell surface protein with hydroquinone (NADH) oxidase and protein disulfide-thiol interchange activities. In general, most forms of the enzyme can utilize either NADH or NADPH equally efficiently. There are many forms of Nox, including Nox 1-5, Dual oxidase 1 and 2 (Duox 1 and 2), as well as p22(phox), p47(phox) and the small G-protein Rac1.

Nox are believed to account for increased levels of ROS in certain cancers. Reactive oxygen-generating Nox enzymes are implicated in the angiogenic switch, and Nox inhibitors have an effect on ang-2 production in vitro and on bEnd.3 tumor growth in vivo. ang-2 production can be inhibited pharmacologically using Nox enzyme inhibitors, which nearly abolishes bEnd.3 hemangioma growth in vivo. Signal-transduction blockade targeting ang-2 production may therefore be useful for treating human hemangiomas in vivo. Journal of Investigative Dermatology advance online publication, 1 Jun. 2006; doi:10.1038/sj.jid.5700413.

With respect to specific Nox enzymes, it has been shown that transfection of Nox1 into a prostate cancer cell line dramatically enhanced tumor growth (Arbiser et al.: PNAS 99:715-720, 2001), and prostate tumors show increased $H_2O_2$ levels. Further, prostate tumors were recently found to show increased levels of Nox1 and hydrogen peroxide (Lim et al., Prostate. 2005 Feb. 1; 62(2):200-7). Nox1-dependent superoxide production has also been shown to control colon adenocarcinoma cell migration (Sadok et al., *Biochim. Biophys. Acta.* 1783(1):23-33 (January 2008). Sadok showed that Nox1 inhibition or down-regulation led to a decrease of superoxide production and alpha 2 beta 1 integrin membrane availability. Thus, there is a correlation between Nox protein levels and ROS in prostate cancer, and increased Nox1/$H_2O_2$ correlates with increased tumorigenicity.

Nox4 is believed to be implicated in inhibition of apoptosis in cancer cells, such as pancreatic cancer cells (Vaquero et al., *J Biol. Chem.* 2004 Aug. 13; 279(33):34643-54). Vaquero suggested that growth factor-induced ROS produced by NAD (P)H oxidase (probably Nox4) protects pancreatic cancer cells from apoptosis, and that transfection with a Nox4 antisense oligonucleotide inhibited NAD(P)H oxidase activity and ROS production in certain pancreatic cells (i.e., MIA PaCa-2 and PANC-1 cells), and stimulated apoptosis in these cells.

Akt, a signaling molecule downstream of PI3K, is known to induce expression of the ROS-generating enzyme Nox4. One study introduced Akt into a radial growth WM35 melanoma in order to test whether Akt overexpression was sufficient to transform the cells from radial growth to vertical growth. Overexpression of Akt led to upregulation of VEGF, increased production of superoxide ROS, and the switch to a more pronounced glycolytic metabolism. Subcutaneous implantation of WM35 cells overexpressing Akt led to rapidly growing tumors in vivo, while vector control cells did not form tumors. Arbiser et al., *J. Clini. Invest.* 117(10): 2762-2765 (2007). This data supports the premise that inhibition of Akt can inhibit downstream production of Nox 4, which then would inhibit superoxide generation, and therefore treat melanoma.

Duox 1 and 2 are the major Nox species in airway endothelia, and are believed to be one of the main sources for reactive oxygen species production in the airway (Luxen et al., *Cancer Res.* 2008 Feb. 15; 68(4):1037-45). Accordingly, inhibition of these enzymes may be useful in treating human lung cancer.

Some authors have characterized Nox as falling into two categories. One is hormone-insensitive and drug-responsive (i.e., by quinine-site inhibitors such as capsaicin or the antitumor sulfonylurea, LY181984), designated "tNox," which is specific to cancer cells. The other is a drug-indifferent constituted form associated with the plasma membrane of non-transformed cells, designated "CNox" (Bruno et al., 1992, Biochem. J. 284:625-628 and Morre and Morre, 1995, Protoplasma 184:188-195).

Cancer cells exhibit both drug-responsive and hormone and growth factor-indifferent (tNox), and drug inhibited and hormone and growth factor dependent (CNox) activities, whereas non-transformed cells exhibit only the drug inhibited hormone- and drug-responsive CNox. Like the tNox of cancer cells, CNox is capable of oxidizing NADH, but has an activity which is modulated by hormones and growth factors. Thus, some authors have theorized that inhibitors of tNox (which are believed to include one or more of the Nox enzymes listed above, such as Nox4) will be useful for treating cancer.

In addition to treating cancer, Nox inhibitors are also expected to have provide therapeutic effects for numerous other inflammatory, degenerative and vascular diseases in which reactive oxygen species have been implicated.

For example, Nox has been reported to have a role in retinal vascular inflammation, as well as ischemia-induced increases in vascular endothelial growth factor (VEGF) and retinal neovascularization (Al-Shabrawey et al., Invest, *Ophthalmol, Vis, Sci.* (2008)). Studies performed using wild type mice, mice lacking Nox2 and mice treated with the NADPH oxidase inhibitor apocynin in models of endotoxemia and streptozotocin-induced diabetes showed that both endotoxemia- and diabetes-induced increases in ICAM-1 expression and leukostasis were significantly inhibited by deletion of Nox2. Apocynin treatment was as effective as deletion of Nox2 in preventing diabetes-induced increases in ICAM-1, leukostasis, and breakdown of the blood-retinal barrier, suggesting that Nox2 is primarily responsible for these early signs of diabetic retinopathy.

Elevated ROS initiate and anti-oxidants inhibit the apoptotic cell loss in the retinal pigment epithelium (Glotkin et al, 2006 IOVS, 47: 4614-4623). This is thought to play a role in the development of dry age-related macular degeneration. Likewise, the use of antioxidants had been shown to reduce the progression to neovascularization in patients with large drusen in AMD (Coleman and Chew, 2007, Curr. Opin. Ophthalmol. 18(3): 220-223).

NADP+ reductases lower the concentration of retinaldehyde and retinoic acid, which in turn protect cells from retinaldehyde-induced cell death (Lee et al., J. Biol. Chem., 282(49)35621-8 (2007). By extension, inhibition of NADPH oxidase can have the same effect as increasing the rate of a NADP+ reductase, and have a beneficial effect on retinal degeneration mediated by retinaldehyde or retinoic acid.

Specific inhibition of NADPH oxidase has been shown to reduce angiogenesis in models of retinopathy of prematurity (Al-Shabraway et al, 2005, Am. J. Pathol. 167(2): 599-607 and Saito et al, 2007, Mol. Vision, 13: 840-853). In addition elevated ROS have been observed in diabetic animals and the elevation correlates with increase VEGF activity. Similarly, oxidative stress is thought to be a significant factor in the development of diabetic retinopathy (Kowluru and Chan, 2007, Expt. Diabetes Res. Article ID 43603).

ROS may have two separate effects in the development of glaucoma. First, increased ROS led to increased cellularity of the trabecular meshwork (and thereby increased intraocular pressure, Sacca et al, 2007, Exp. Eye Res. 84(3): 389-399). Over time increased reactive oxygen species are also thought to stimulate apoptosis of retinal ganglion cells (Tezel, 2006, Prog. Retin. Eye Res. 25(5): 490-513), the anatomic basis of visual field loss.

In non-ocular cutaneous tissues, NADPH oxidase from pollen has been shown to perpetuate the allergic response Inhibition of NADPH oxidase reduces mast cell degranulation and may be useful in allergic eye disease (Nishikawa et al, 2007, BBRC, 362(2): 504-509).

Although direct experimental evidence that inhibition of NADPH oxidase will provide a therapeutic effect in the some of the eye diseases mentioned is lacking, NADPH oxidase inhibition can be expected to alter the cellular redox balance and thus may be therapeutic in the various condition by indirect means.

NADPH oxidase inhibitors may also be effective for the treatment of dry eye based on the observation that NADPH oxidase is constituitively expressed in corneal epithelial and stromal cells (O'Brien et al, 2006, IOVS, 47: 853-863). The authors suggest that the production of superoxide anion may play a role in inflammation of the cornea.

With respect to the role of specific Nox enzymes in inflammatory disorders, Nox2-containing NADPH oxidase and Akt activation are believed to play a key role in angiotensin II-induced cardiomyocyte hypertrophy (Physiol. Genomics 26: 180-191, 2006).

Accordingly, Nox are believed to be responsible for increased levels of ROS in some cancers and inflammatory disorders, and treatment with appropriate inhibitors may be useful in treating such cancers and inflammatory disorders.

There remains a need for treatment of cancer that does not have the adverse effects generally caused by the non-selectivity of conventional chemotherapeutic agents. There further remains a need to have additional treatments for inflammatory, degenerative and vascular diseases in which a reactive oxygen species has been implicated. The present invention provides such compounds, compositions and methods.

SUMMARY OF THE INVENTION

Compounds, pharmaceutical compositions including the compounds, and methods of preparation and use thereof are disclosed. In one embodiment, the compounds are fulvene and/or fulvalene analogs, which can be formed by reacting a cyclopentadienyl anion with one or more ketone or aldehyde groups on a suitable intermediate. In another embodiment, the compounds are fulvene and/or fulvene analogues which can be formed by reacting a fulvene and/or fulvalene-containing carboxylic acid (or acid halide or anhydride thereof) with a hydroxyl, thiol, or amine group on a sugar, nucleoside, nucleotide, or amino acid, or oligonucleotides and peptides including the nucleotides or amino acids.

Representative compounds include fulvene and/or fulvalene analogues of steroids and steroid precursors, such as cholesterol, progesterone, testosterone, or estrogen; dyes such as indigo and benzophenones; curcumin and aldehyde and ketone-containing curcumenes.

The synthesis, characterization and an evaluation of the anti-tumor potential of these fulvene and/or fulvalene-containing compounds is also disclosed.

While not wishing to be bound by a particular theory, it is believed that the compounds function by one or more of the following mechanisms:
a) inhibiting all forms of Nox,
b) specifically inhibiting Nox 1-5,
c) specifically inhibiting Nox 2 and/or Nox 4 (the latter of which is more prevalent in cancer cells than normal cells),
d) inhibiting a Nox enzyme that is more prevalent in cancer cells than normal cells, hereinafter referred to as tNox,
e) inhibiting ROS, and
f) stimulating superoxide scavengers, such as scavenger enzyme systems catalase, superoxide dismutase I (Zn2+/Cu2+ SOD) and II (MN-SOD), and glutathione peroxidase.

Evidence that the compounds can inhibit ROS is demonstrated herein in the working examples, which show that electron spin resonance spectra show that when the compounds are added to superoxide dismutase, they alter the spectra of the superoxide dismutase, and appear to be converted to a free radical.

Treatment with one or more of these compounds selectively kills cancer cells, without killing healthy cells, thus providing a selective anti-cancer therapy. Most importantly, these compounds are potent against cancer cells that have become metastacized. As discussed above, the mechanism for killing the cancer cells may involve inhibition of tNOX, without significantly affecting CNox, thereby effectively inhibiting cell proliferation, particularly in metastacized tumors, or the inhibition of any of the Nox enzymes, such as Nox4, which is prevalent in cancer cells. That is, in some embodiments, the Nox is one that is selectively expressed in cancer cells over normal cells, and in other embodiments, the Nox is one that is expressed in higher concentrations in cancer cells than in normal cells.

The pharmaceutical compositions include an effective amount of the compounds described herein, along with a pharmaceutically acceptable carrier or excipient. When employed in effective amounts, the compounds can act as a therapeutic agent to prevent and/or treat a wide variety of cancers, particularly metasticized cancers, and are believed to be both safe and effective in this role. Representative cancers that can be treated and/or prevented include melanoma, leukemia, non-small cell lung, colon, central nervous system (CNS), renal, ovarian, breast and prostate cancer. Additional pharmaceutical compositions may be useful for the treatment of ocular diseases.

The foregoing and other aspects of the present invention are explained in detail in the detailed description and examples set forth below.

DETAILED DESCRIPTION OF THE INVENTION

Figure 1:
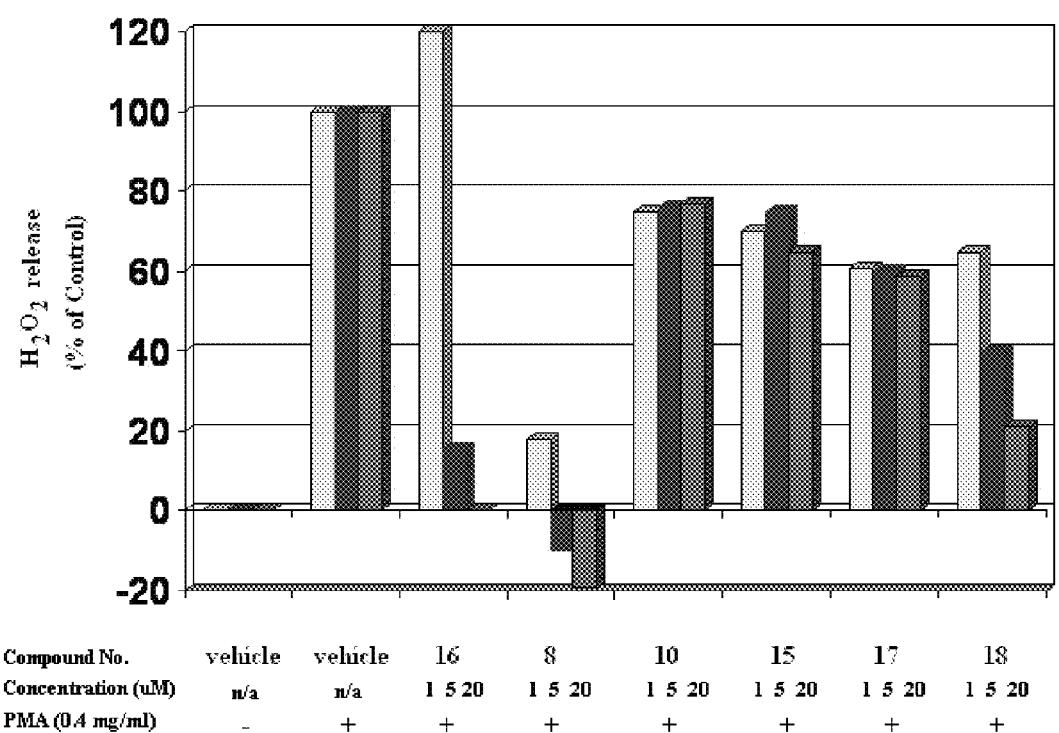
FIG. 1 is a graphic representation of inhibition of Nox2 activity by various test compounds as determined by $H_2O_2$ production in PMA-stimulated Cos-phox cells treated with different concentrations of a vehicle control or the various test compounds.

Compounds, pharmaceutical compositions including the compounds, and methods of preparation and use thereof are disclosed.

The following definitions will be useful in understanding the metes and bounds of the invention as described herein.

As used herein, "alkyl" refers to straight chain or branched alkyl radicals including $C_1$-$C_8$, preferably $C_1$-$C_5$, such as methyl, ethyl, or isopropyl; "substituted alkyl" refers to alkyl radicals further bearing one or more substituent groups such as hydroxy, alkoxy, aryloxy, mercapto, aryl, heterocyclo, halo, amino, carboxyl, carbamyl, cyano, and the like; "alkenyl" refers to straight chain or branched hydrocarbon radicals including $C_1$-$C_8$, preferably $C_1$-$C_5$ and having at least one carbon-carbon double bond; "substituted alkenyl" refers to alkenyl radicals further bearing one or more substituent groups as defined above; "cycloalkyl" refers to saturated or unsaturated, non-aromatic, cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above.

I. Compounds

The compounds are fulvene and/or fulvalene analogs, prodrugs or metabolites of these compounds, and pharmaceutically acceptable salts thereof. In one embodiment, the compounds generally fall within one of the formulas provided below:

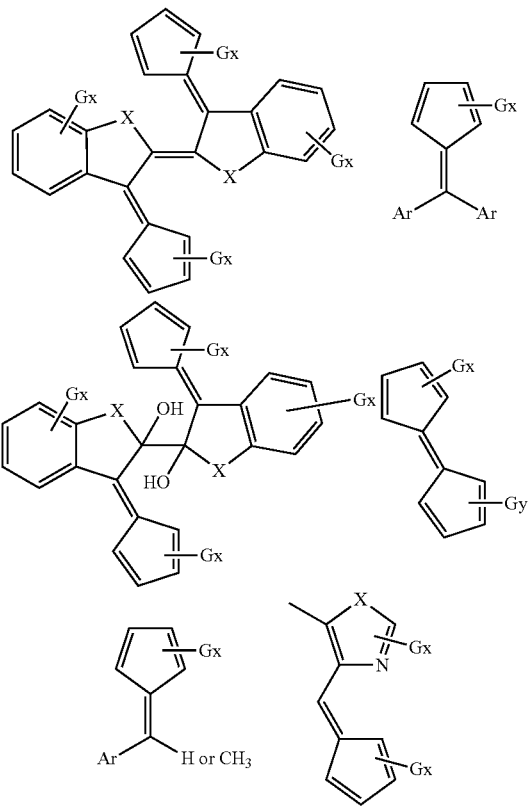

wherein Ar is the same or different aryl or heteroaryl ring, optionally substituted with one or more substituents, G, as described herein wherein:
X is O, S, $CH_2$, or NR', where each R' is, individually, hydrogen, $C_{1-6}$ alkyl, cycloalkyl, heterocyclyl, aryl, or arylalkyl (such as benzyl); and
the aryl or heteroaryl rings can be substituted at any free position with H or a substituent, G, as described herein, and x and y are integers between 0 and 3.

In other embodiments, the compounds are ether, thioether, or amine derivatives of compounds which originally included a hydroxyl, thiol, or amine group, where this group has been reacted with a compound that includes a fulvene or fulvalene moiety, and a carboxylic acid or an activated carboxylic acid moiety, as described herein. One fulvene-containing carboxylic acid is shown below:

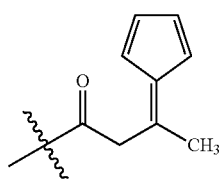 [SMILES: *C(=O)CC(C)=C1C=CC=C1]

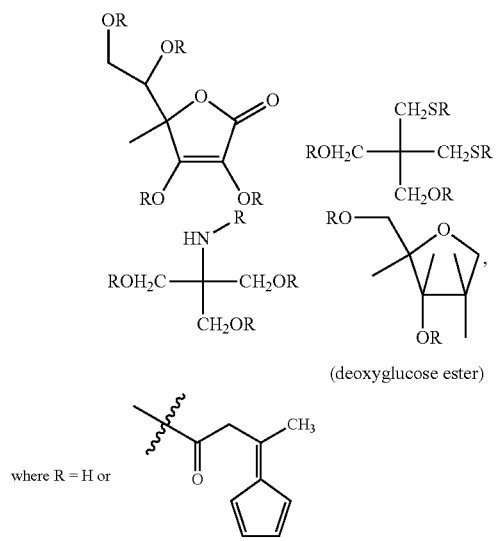

where the carbonyl group is attached to a hydroxyl, thiol, or amine group on an intermediate to form an ester, thiolester, or amide linkage. Analogous compounds can be prepared, for example, by using different keto- or aldehyde-containing carboxylic acids, by analogous reaction with cyclopentadienyl anion.

Representative hydroxyl, thiol, and amine-containing moieties that can be used to prepare the compounds described herein, by reaction with a fulvene- or fulvalene-containing carboxylic acid, acid halide, or anhydride, include natural or synthetic sugars, polyols, polyalkylene glycols, such as polyethylene glycol, nucleosides and nucleotides (for example, by reaction with the 3' and/or 5'-hydroxy groups on these compounds), short (i.e., 25 mer or less) oligonucleotides including these nucleosides, hydroxyl, thiol, and/or amine-containing amino acids, peptides and proteins including these amino acids, and compounds of the following formulas:

or another fulvene- or fulvalene-containing carboxylic acid moiety or activated carboxylic acid moiety as described above, with the proviso that at least one of R is other than H.

Representative substituents, G, include $C_{1-6}$ alkyl (including cycloalkyl), alkenyl, heterocyclyl, aryl, heteroaryl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", and —NR'SO$_2$R", where R' and R" are individually hydrogen, $C_{1-6}$ alkyl, cycloalkyl, heterocyclyl, aryl, or arylalkyl (such as benzyl);

The compounds can occur in varying degrees of enantiomeric excess, and racemic mixtures can be purified using known chiral separation techniques.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, dichloroacetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

Representative compounds include the following:

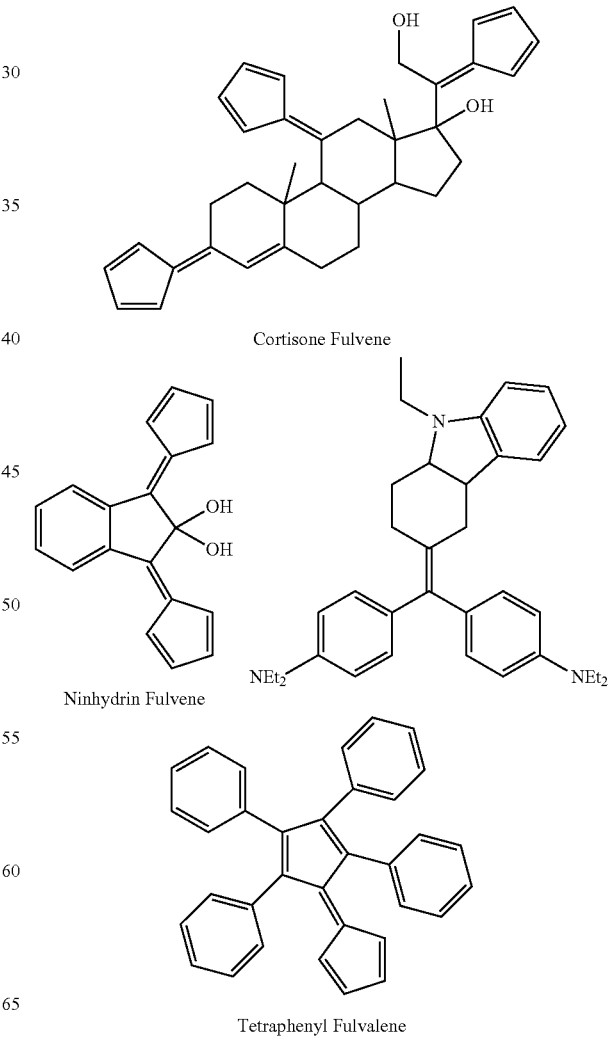

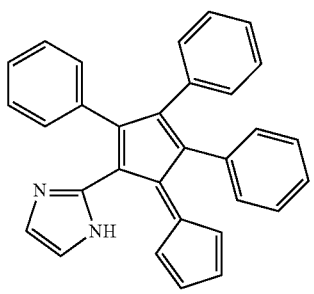
Triphenylimidazolyl Fulvalene
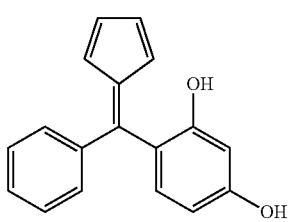
Dihydroxybenzophenone Fulvene
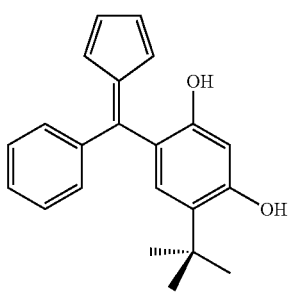
Dihydroxy-t-butyl-benzophenone Fulvene
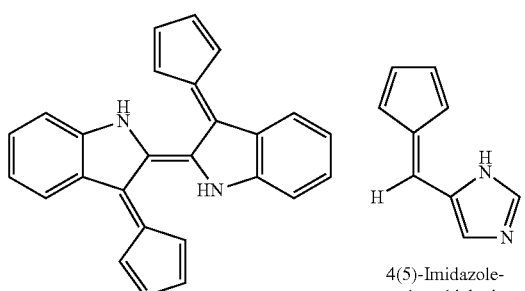
Indigo Fulvene
4(5)-Imidazole-carboxaldehyde Fulvene
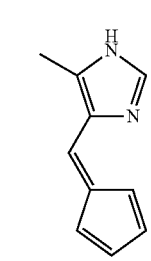
4-(cyclopenta-2,4-dienylidenemethyl)-5-methyl-1H-imidazole
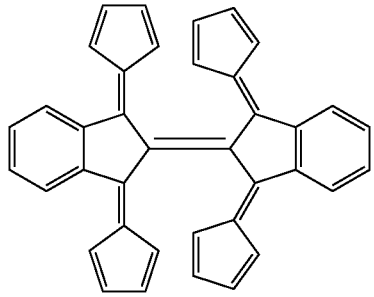
Hydrindantin Fulvene
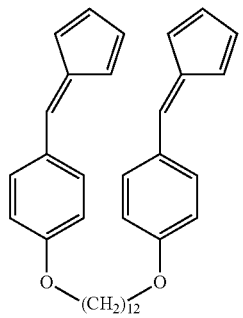
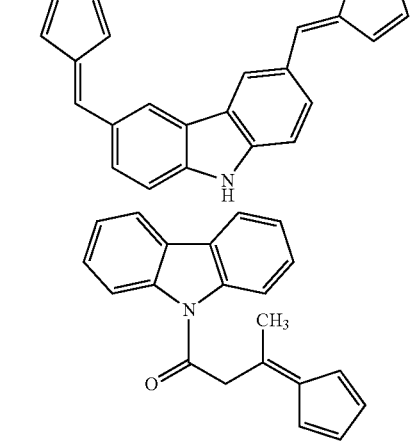
curcumin Fulvene
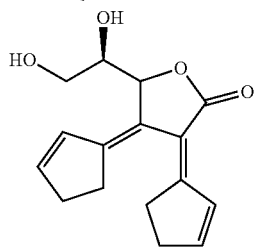
Esteronic Fulvene
L-ascorbic acid fulvene

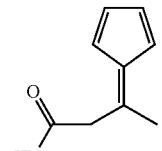
2-butyl-5-chloro-1H-imidazole-4-fulvene
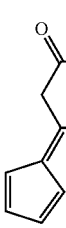
Silymarin fulvene
Bipyridine fulvene   1-Methyl-2-imidazole fulvene
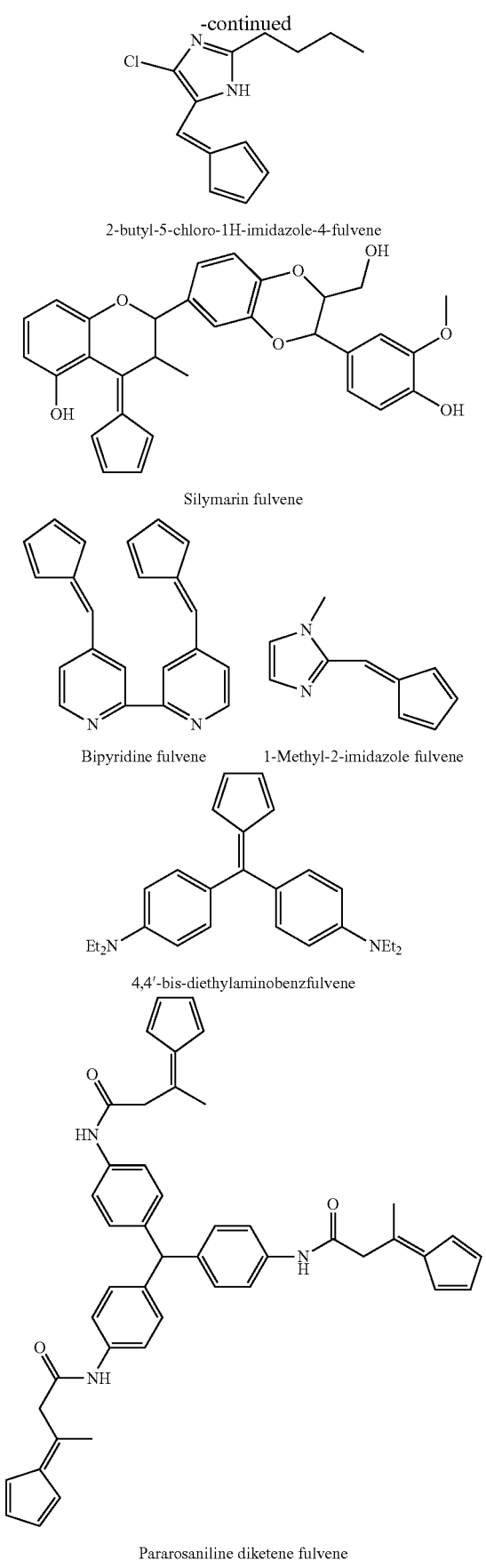
4,4'-bis-diethylaminobenzfulvene
Pararosaniline diketene fulvene
Pararosaniline diketene fulvene
(oxidized form)
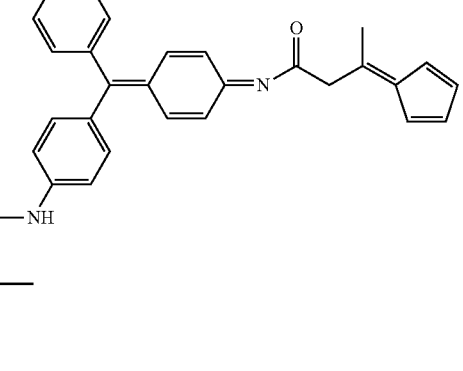
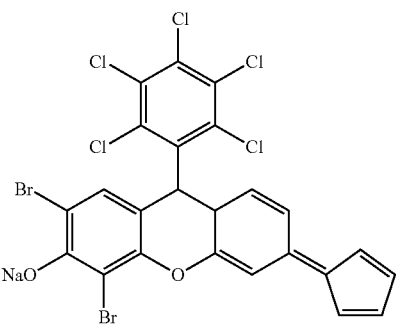
Phloxine B fulvene
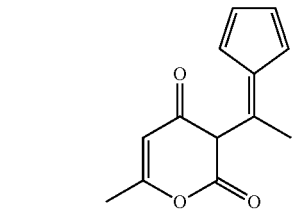
Dehydroacetic acid fulvene
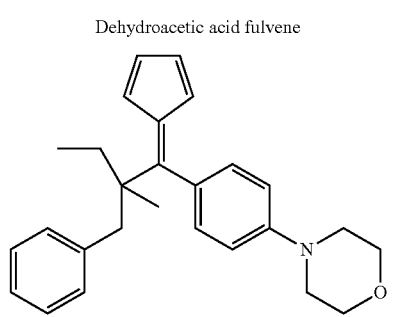
Irgacure Fulvene

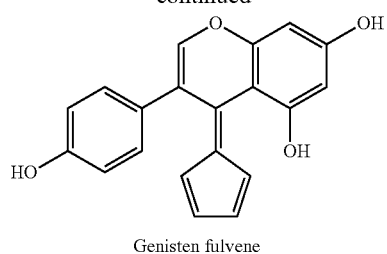
Genisten fulvene
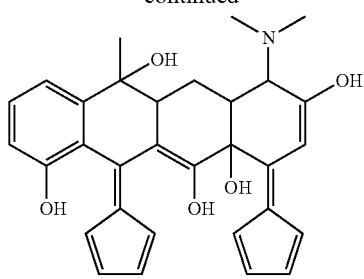
Tetracycline fulvene
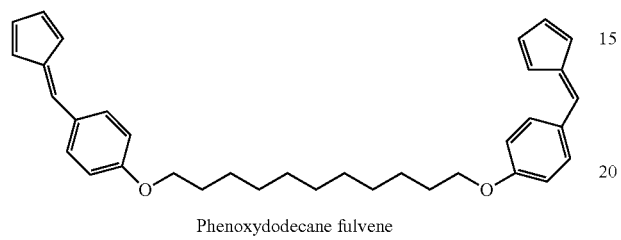
Phenoxydodecane fulvene
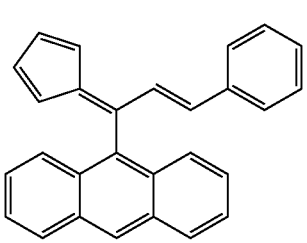
(E)-9-(1-(cyclopenta-2,4-dienylidine)-3-phenyl(allyl)anthracene
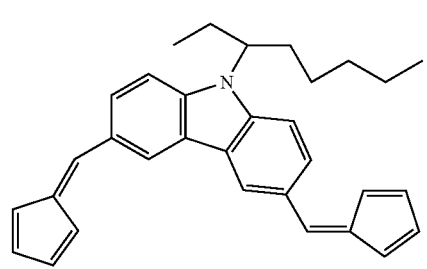
N-2-(ethylhexyl)-carbazole-4,4'-fulvene
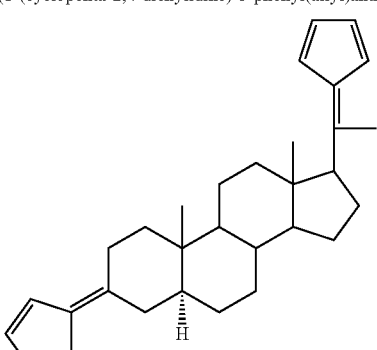
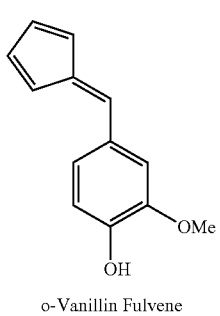
o-Vanillin Fulvene
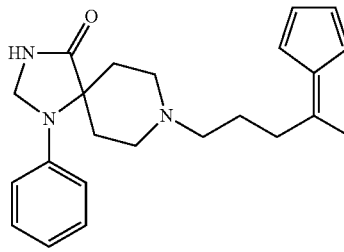
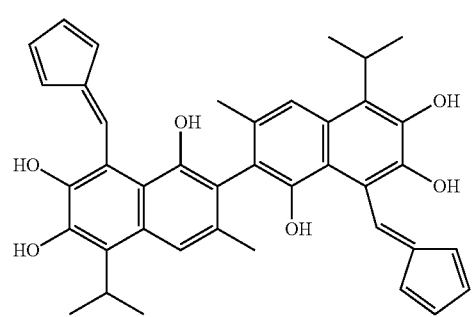
Gossypol fulvnene
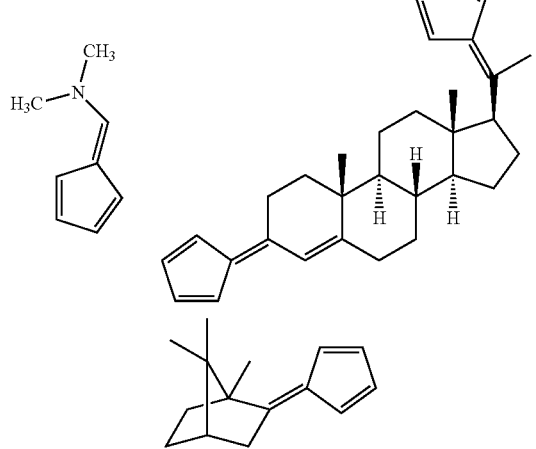

15
-continued
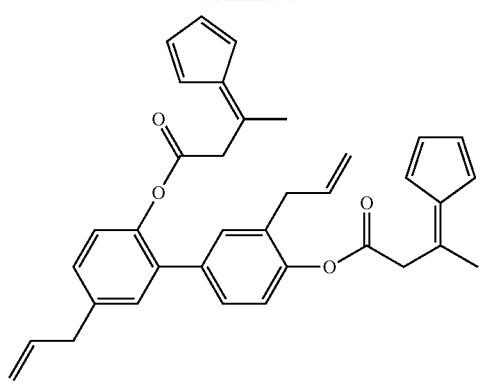
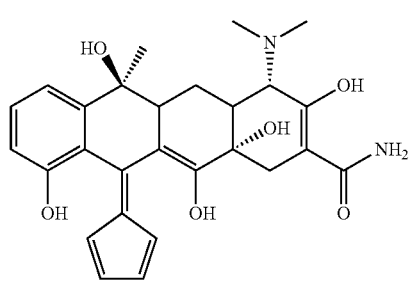
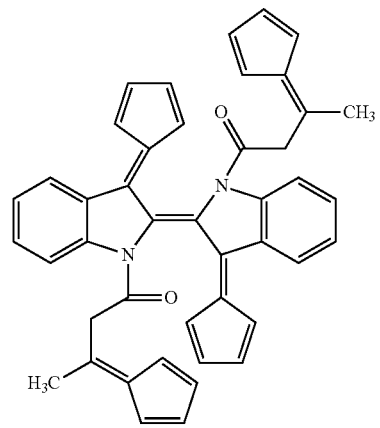
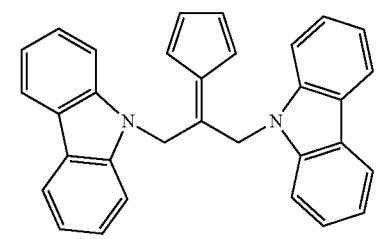
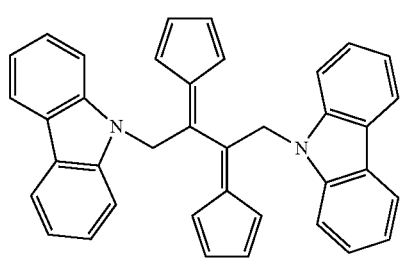
16
-continued
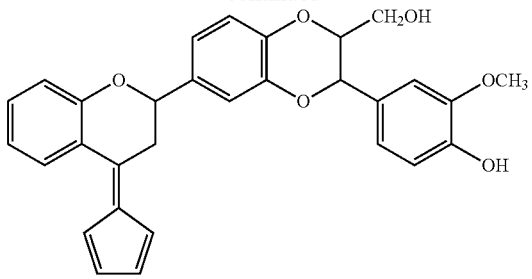
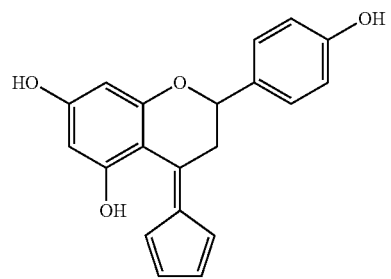
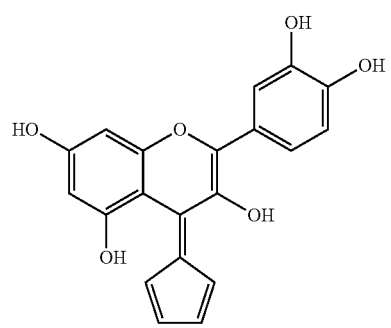
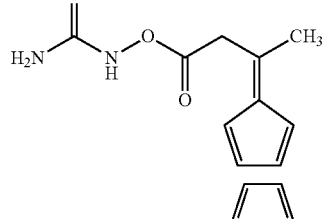
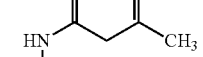
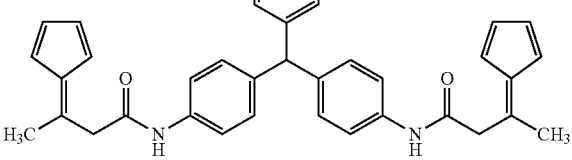
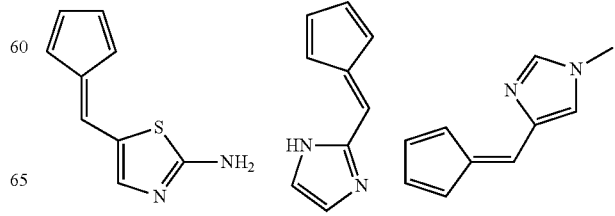

17
-continued

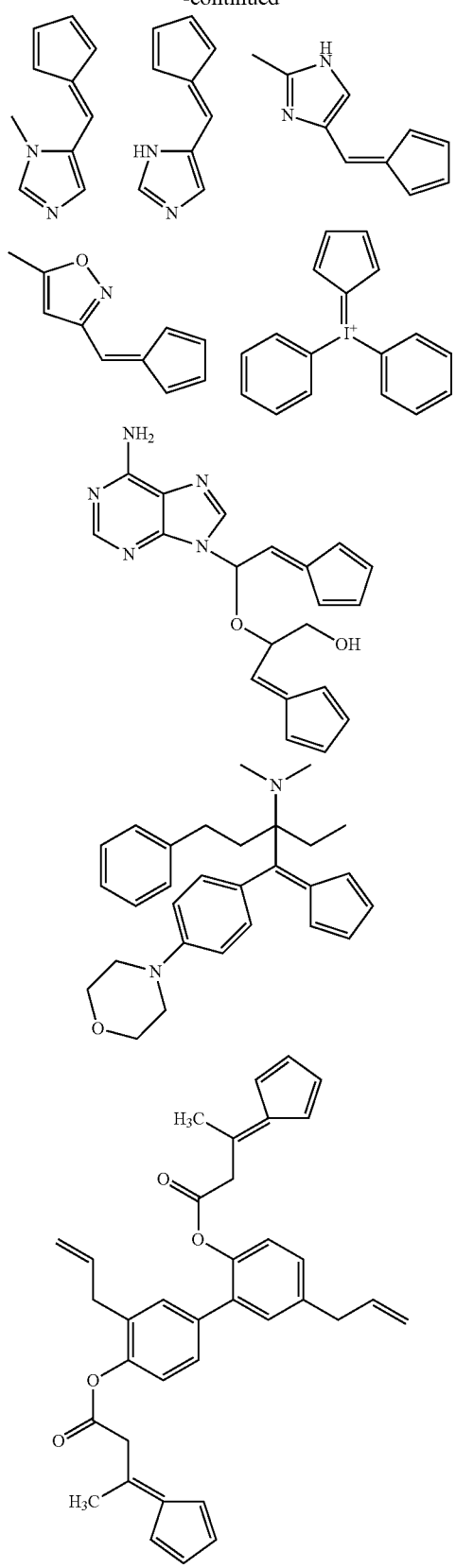

The compound identified above as indigo fulvene is also referred to herein as "Fulvene-5."

18

If desired, certain of these compounds can be rendered more hydrophobic by substituting a $C_{1-6}$ alkyl, cycloalkyl, heterocyclyl, aryl, or arylalkyl moiety for hydrogen, or a cycloalkyl, heterocyclyl, aryl, or arylalkyl moiety for an alkyl moiety, on a nitrogen atom in the structure. Examples include the following:

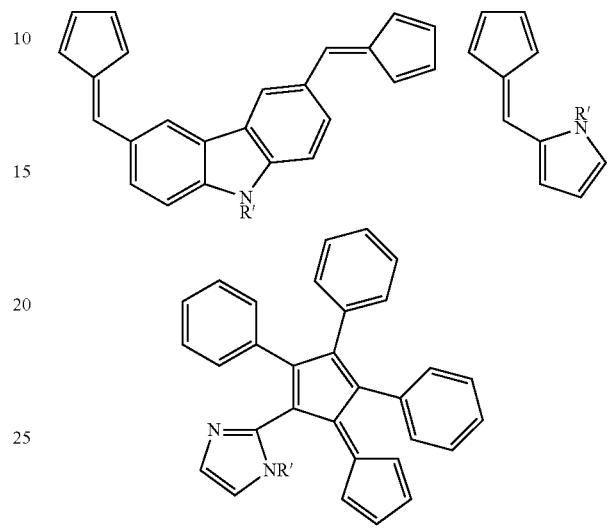

II. Methods of Preparing the Compounds

In some embodiments, the compounds can be prepared by reacting sodium cyclopentadienide with any aldehyde or ketone. Using this approach, numerous fulvenes can be made from readily available ketone- or aldehyde-containing starting materials.

Representative aldehydes and ketones are provided below:

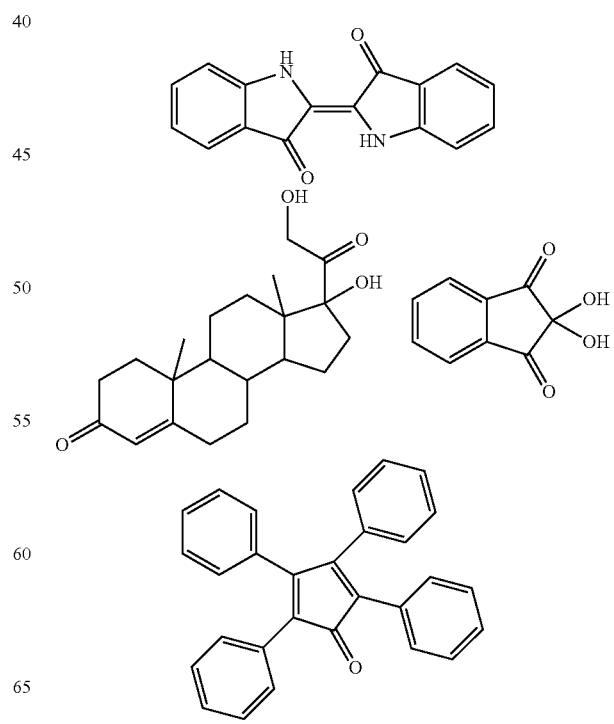

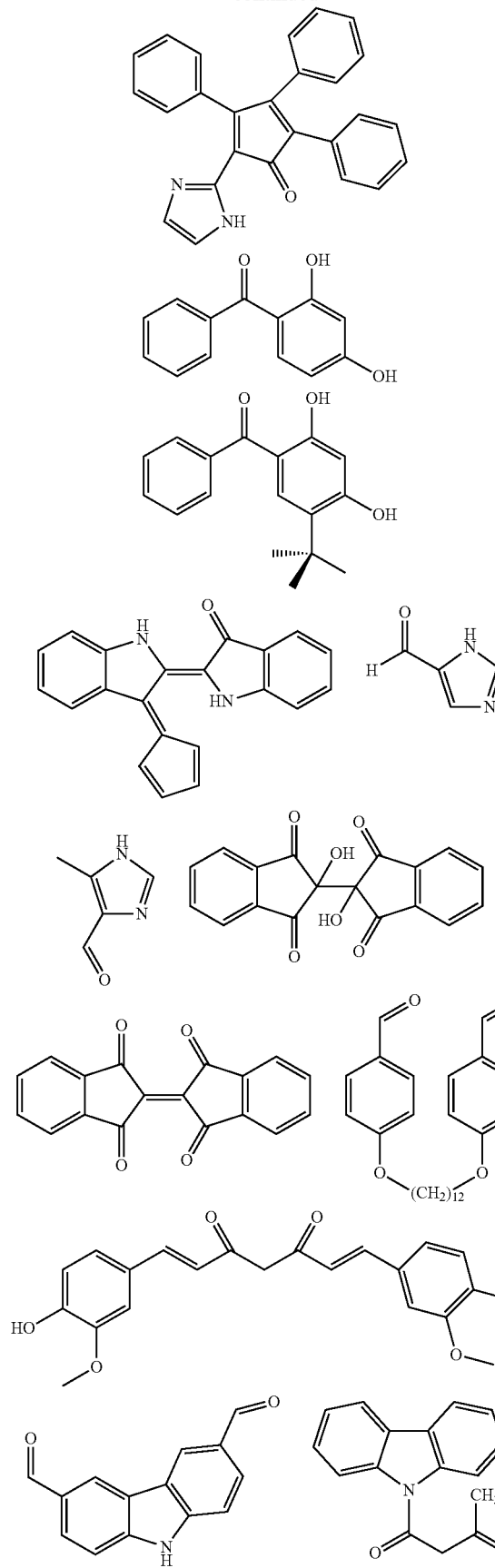

21
-continued
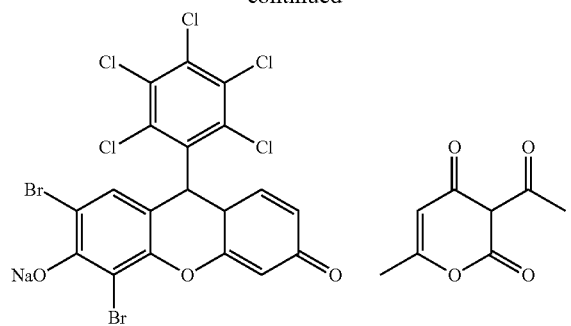
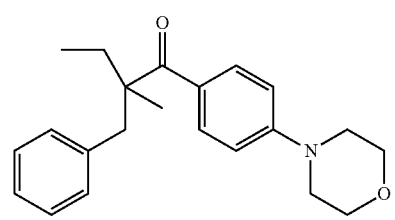
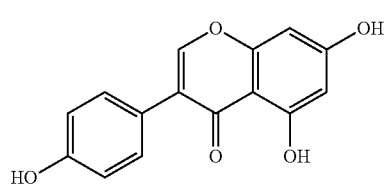
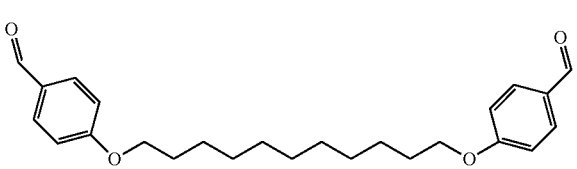
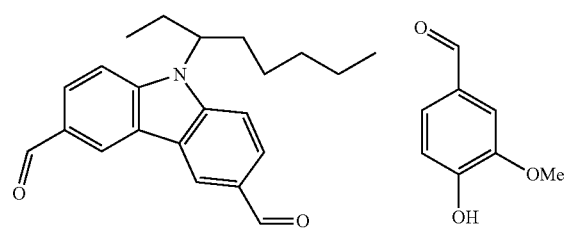
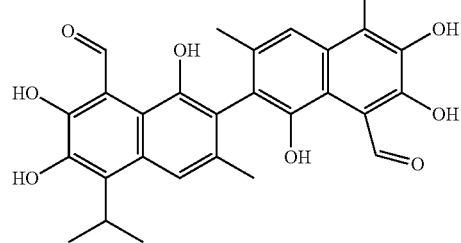
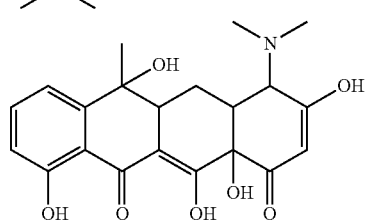
22
-continued
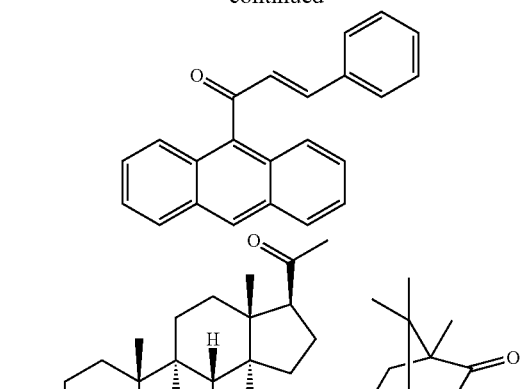
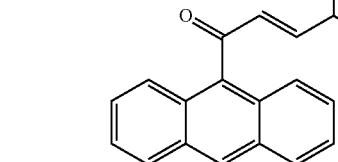
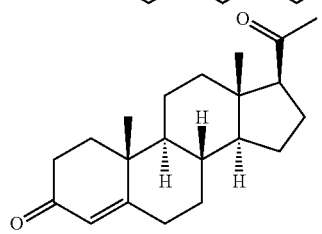
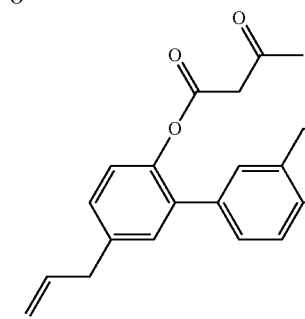
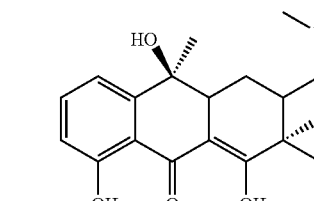
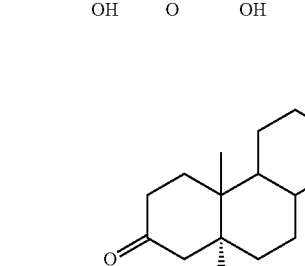
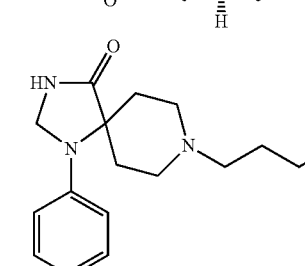
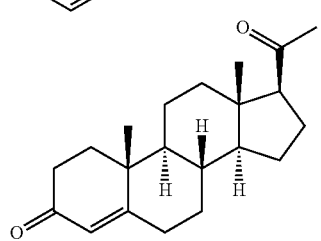

23
-continued
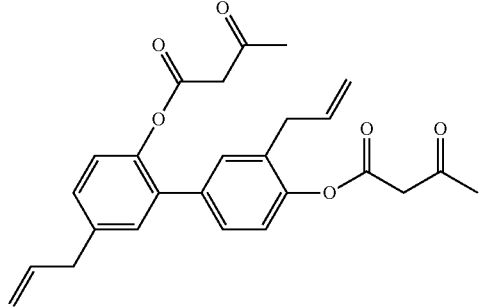
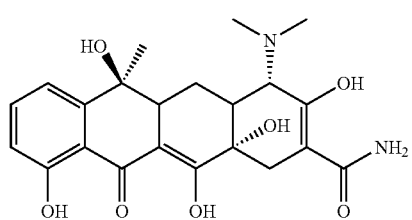
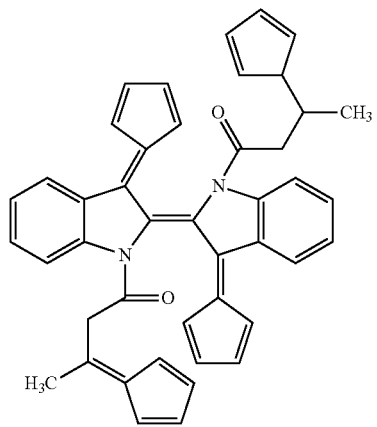
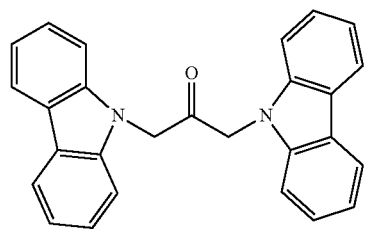
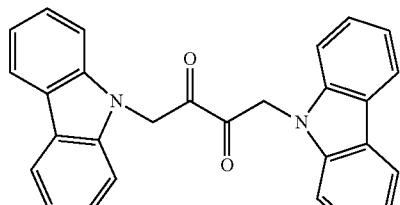
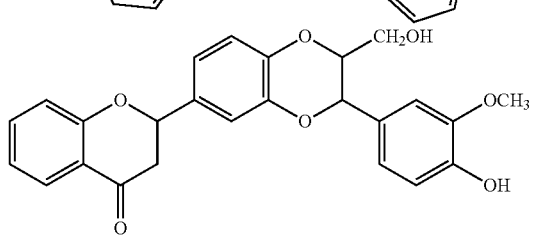
24
-continued
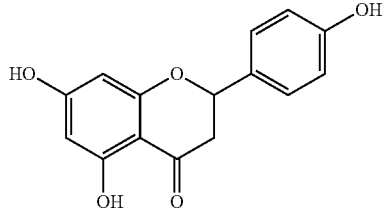
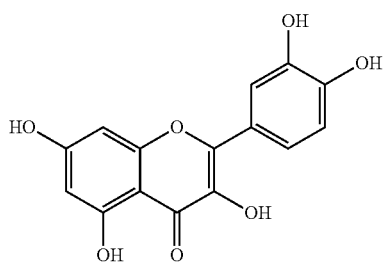
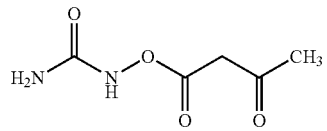
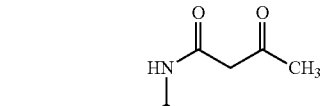
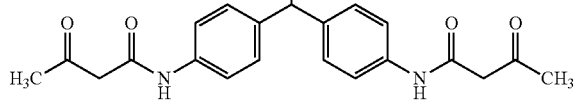
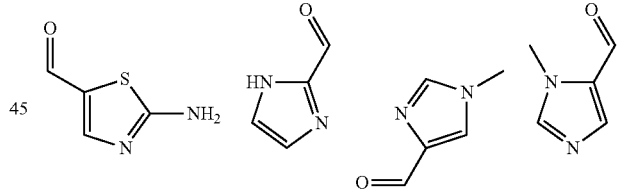

-continued

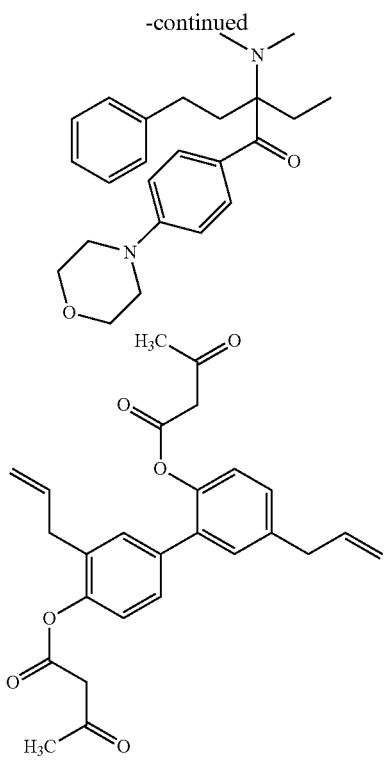

wherein any of the aryl/heteroaryl rings can be substituted with one or more substituents as described herein, and amines (i.e., —NH groups) can be substituted with R' groups as described herein.

In other embodiments, the compounds are prepared by reacting a hydroxyl, thiol, or amine group with a compound that includes a fulvene or fulvalene moiety, and a carboxylic acid or an activated carboxylic acid moiety.

Generally, the hydroxyl, thiol, or amine group is reacted with either a fulvene- or fulvalene-containing carboxylic acid or an activated derivative thereof (e.g., an acid chloride or anhydride), in the presence of dehydrating agents and/or bases. A variety of conditions are possible.

A carboxylic acid can be coupled to a hydroxyl or ester group directly, with an acid catalyst and subsequent formation of water (typically removed by azeotropic distillation), or by reaction with an acid halide or anhydride, typically in the presence of a tertiary amine such as triethylamine. The resulting compound has an ester or thiolester linkage, and the fulvene and/or fulvalene moiety is attached via this linkage.

Intermediates with a free amine functionality can be coupled to a carboxylic acid-containing, fulvene or fulvalene-containing moiety using any one of various agents used for forming amide bonds (for instance, those used in peptide synthesis). Such reagents include N,N'-dicyclohexylcarbodiimide (DCC), (benzotriazol-1-yloxy)tris(dimethylamino) phosphonium hexafluorophosphate (BOP), (benzotriazol-1-yloxy)tripyrrolidinophosphonium hexafluorophosphate (PyBOP), O-(benzotriazol-1-yl)-N,N,N',N'-bis(tetramethylene)uronium hexafluorophosphate (HBPyU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), and (1-ethyl-3-(3-dimethylaminopropyl)carbodiimide) (EDCI) with 1-hydroxybenzotriazole (HOBt). In some cases these reagents are commercially available as polymer supported modifications, which greatly facilitate isolation of coupling products. An example of such a reagent is polystyrene bound N,N'-dicyclohexylcarbodiimide (PS-DCC).

Acid halides can be prepared, for example, by reacting the carboxylic acid-containing moeity with any of various reagents, such as thionyl chloride or oxalyl chloride. The reaction between the acid chloride and the carboxylic acid is typically performed in the presence of a tertiary amine, usually a hindered one.

Typically, after ester, thiolester, or amide bond formation, any protecting groups (e.g., a tert-butoxycarbonyl group or a benzyl group) are removed to generate the desired compounds. Protecting groups, and methods for their removal, are well known to those of skill in the art, and are described for example, in T. W. Greene and P. G. M. Wuts, Protective Groups in Organic Synthesis, 3$^{rd}$ Edition, John Wiley & Sons, New York (1999).

The fulvene-containing and/or fulvalene-containing carboxylic acids used to make compounds described herein are either commercially available, or can be prepared from commercially available starting materials. Those that are not commercially available can be made by a variety of synthetic methodologies, related to the particular moieties and the particular substitution desired. The variation in synthetic methodology will be readily apparent to those of skill in the art of organic synthesis.

For example, one fulvene-containing and/or fulvalene-containing carboxylic acid is shown below:

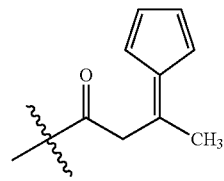 [SMILES: *C(=O)CC(C)=C1C=CC=C1]

where the carbonyl group is attached to a hydroxyl, thiol, or amine group on an intermediate to form an ester, thiolester, or amide linkage. This intermediate can be prepared, for example, by reacting a suitably protected 3-keto butyric acid (or the corresponding butyrate salt) with cyclopentadienyl anion to form the fulvene ring. The carboxylate salt can be acidified to reform the carboxylic acid moiety, which can be further reacted to form an anhydride or acid halide, if desired. This carboxylic acid, acid halide, or acid anhydride intermediate can be used to form a fulvene analogue of virtually any hydroxyl, thiol, or amine-containing compounds, using the esterification, thiolesterification, or amidation chemistry described above.

The above intermediate is just one of a number of compounds that can be used to incorporate a fulvene or fulvalene moiety onto a compound. Analogous compounds can be prepared, for example, by using different keto- or aldehyde-containing carboxylic acids, by analogous reaction with cyclopentadienyl anion.

Representative hydroxyl, thiol, and amine-containing moieties that can be used to prepare the compounds described herein, by reaction with a fulvene- or fulvalene-containing carboxylic acid, acid halide, or anhydride, are described below.

Natural or synthetic sugars, polyols, polyalkylene glycols, such as polyethylene glycol, nucleosides and nucleotides (for example, by reaction with the 3' and/or 5'-hydroxy groups on these compounds), short (i.e., 25 mer or less) oligonucleotides including these nucleosides, hydroxyl, thiol, and/or amine-containing amino acids, peptides and proteins including these amino acids, and compounds of the following formulas:

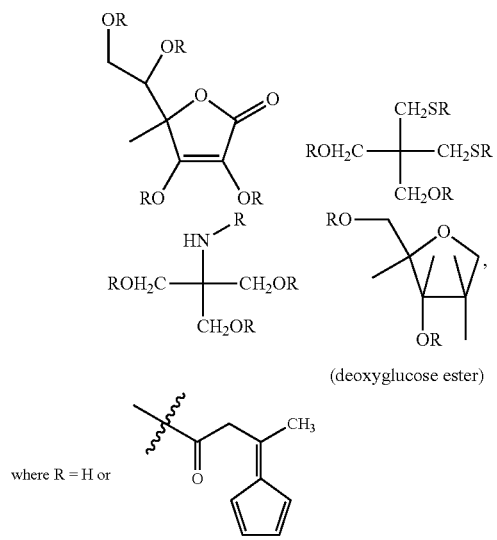

(deoxyglucose ester)

where R = H or or another fulvene- or fulvalene-containing carboxylic acid moiety or activated carboxylic acid moiety as described above, with the proviso that at least one of R is other than H.

Those skilled in the art will readily understand that incorporation of other substituents onto the cyclopentadiene ring used as a starting material to prepare the fulvenes/fulvalenes, and other positions in the fulvene/fulvalene framework, can be readily realized. Such substituents can provide useful properties in and of themselves or serve as a handle for further synthetic elaboration.

Substituents typically can be added to a cyclopentadiene before forming the sodium cyclopentadienide (i.e., by addition of base) that is reacted with a suitable ketone or aldehyde to form the compounds described herein, or to form the fulvene/fulvalene containing carboxylic acid/acid halide/acid anhydride reacted with hydroxyl, thiol, or amine groups to form the compounds described herein.

For example, diazocyclopentadiene can be prepared using the techniques in Cram and Partos, Electrophilic Substitution and Other Reactions of Diazocyclopentadiene, J.A.C.S. p. 1273-1277 (1962).

Diazocyclopentadiene can be halogenated using various known procedures, which vary depending on the particular halogen. Examples of suitable reagents include bromine/water in concentrated HBr, thionyl chloride, pyr-IC1, fluorine and Amberlyst-A A number of other analogs, bearing substituents in the diazotized position of the diazocyclopentadiene, can be synthesized from the corresponding amino compounds, via the diazocyclopentadiene intermediate. The diazocyclopentadiene can be prepared using known chemistry, for example, as described above.

Nitration of the diazocyclopentadiene results in two isomers, the 2-nitro and 3-nitro cyclopentadiene compounds. Benzenediazonium tetrafluoroborate leads to 2-substitution products, whereas bromination provides tetrabromodiazocyclopentadiene. Mercuration with mercury iodide can provide 2,5-di-iododiazocyclopentadiene.

The nitro derivatives can be reduced to the amine compound by reaction with a nitrite salt, typically in the presence of an acid. Other substituted analogs can be produced from diazonium salt intermediates, including, but are not limited to, hydroxy, alkoxy, fluoro, chloro, iodo, cyano, and mercapto, using general techniques known to those of skill in the art. For example, hydroxy-fulvene analogues can be prepared by reacting the diazonium salt intermediate with water, protecting the resulting hydroxyl group, forming the cyclopentadienyl anion, and reacting it with a suitable aldehyde or ketone. Likewise, alkoxy fulvene analogues can be made by reacting the diazocyclopentadiene with alcohols. The diazocyclopentadiene can also be used to synthesize cyano or halo compounds, as will be known to those skilled in the art. Mercapto substitutions can be obtained using techniques described in Hoffman et al., *J. Med. Chem.* 36: 953 (1993). The mercaptan so generated can, in turn, be converted to an alkylthio substitutent by reaction with sodium hydride and an appropriate alkyl bromide. Subsequent oxidation would then provide a sulfone. Acylamido analogs of the aforementioned compounds can be prepared by reacting the corresponding amino compounds with an appropriate acid anhydride or acid chloride using techniques known to those skilled in the art of organic synthesis.

Hydroxy-substituted analogs can be used to prepare corresponding alkanoyloxy-substituted compounds by reaction with the appropriate acid, acid chloride, or acid anhydride. Likewise, the hydroxy compounds are precursors of both the aryloxy and heteroaryloxy via nucleophilic aromatic substitution at electron deficient aromatic rings. Such chemistry is well known to those skilled in the art of organic synthesis. Ether derivatives can also be prepared from the hydroxy compounds by alkylation with alkyl halides and a suitable base or via Mitsunobu chemistry, in which a trialkyl- or triarylphosphine and diethyl azodicarboxylate are typically used. See Hughes, *Org. React.* (*N.Y.*) 42: 335 (1992) and Hughes, *Org. Prep. Proced. Int.* 28: 127 (1996) for typical Mitsunobu conditions.

Cyano-substituted analogs can be hydrolyzed to afford the corresponding carboxamido-substituted compounds. Further hydrolysis results in formation of the corresponding carboxylic acid-substituted analogs. Reduction of the cyano-substituted analogs with lithium aluminum hydride yields the corresponding aminomethyl analogs. Acyl-substituted analogs can be prepared from corresponding carboxylic acid-substituted analogs by reaction with an appropriate alkyllithium using techniques known to those skilled in the art of organic synthesis.

Carboxylic acid-substituted analogs can be converted to the corresponding esters by reaction with an appropriate alcohol and acid catalyst. Compounds with an ester group can be reduced with sodium borohydride or lithium aluminum hydride to produce the corresponding hydroxymethyl-substituted analogs. These analogs in turn can be converted to compounds bearing an ether moiety by reaction with sodium hydride and an appropriate alkyl halide, using conventional techniques. Alternatively, the hydroxymethyl-substituted analogs can be reacted with tosyl chloride to provide the corresponding tosyloxymethyl analogs, which can be converted to the corresponding alkylaminoacyl analogs by sequential treatment with thionyl chloride and an appropriate alkylamine. Certain of these amides are known to readily undergo nucleophilic acyl substitution to produce ketones.

Hydroxy-substituted analogs can be used to prepare N-alkyl- or N-arylcarbamoyloxy-substituted compounds by reaction with N-alkyl- or N-arylisocyanates. Amino-substituted analogs can be used to prepare alkoxycarboxamido-substituted compounds and urea derivatives by reaction with alkyl chloroformate esters and N-alkyl- or N-arylisocyanates, respectively, using techniques known to those skilled in the art of organic synthesis.

Similarly, benzene rings (and pyridine, pyrimidine, pyrazine, and other heteroaryl rings) can be substituted using known chemistry, including the reactions discussed above. For example, the nitro group on nitrobenzene can be reacted with sodium nitrite to form the diazonium salt, and the diazonium salt manipulated as discussed above to form the various substituents on a benzene ring.

III. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more of the fulvene and/or fulvalene analogues described herein, and/or pharmaceutically acceptable salts thereof. Optically active compounds can be employed as racemic mixtures, as pure enantiomers, or as compounds of varying enantiomeric purity.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

The compounds can be incorporated into drug delivery devices such as nanoparticles, microparticles, microcapsules, and the like. Representative microparticles/nanoparticles include those prepared with cyclodextrins, such as pegylated cyclodextrins, liposomes, including small unilamellar vesicles, and liposomes of a size designed to lodge in capillary beds around growing tumors. Suitable drug delivery devices are described, for example, in Heidel J D, et al., Administration in non-human primates of escalating intravenous doses of targeted nanoparticles containing ribonucleotide reductase subunit M2 siRNA, Proc Natl Acad Sci USA. 2007 Apr. 3; 104(14):5715-21; Wongmekiat et al., Preparation of drug nanoparticles by co-grinding with cyclodextrin: formation mechanism and factors affecting nanoparticle formation, Chem Pharm Bull (Tokyo). 2007 March; 55(3):359-63; Bartlett and Davis, Physicochemical and biological characterization of targeted, nucleic acid-containing nanoparticles, Bioconjug Chem. 2007 March-April; 18(2): 456-68; Villalonga et al., Amperometric biosensor for xanthine with supramolecular architecture, Chem Commun (Camb). 2007 Mar. 7; (9):942-4; Defaye et al., Pharmaceutical use of cyclodextrines: perspectives for drug targeting and control of membrane interactions, Ann Pharm Fr. 2007 January; 65(1):33-49; Wang et al., Synthesis of Oligo(ethylenediamino)-beta-Cyclodextrin Modified Gold Nanoparticle as a DNA Concentrator; Mol. Pharm. 2007 March-April; 4(2): 189-98; Xia et al., Controlled synthesis of Y-junction polyaniline nanorods and nanotubes using in situ self-assembly of magnetic nanoparticles, J Nanosci Nanotechnol., 2006 December; 6(12):3950-4; and Nijhuis et al., Room-temperature single-electron tunneling in dendrimer-stabilized gold nanoparticles anchored at a molecular printboard, Small. 2006 December; 2(12):1422-6.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where cancer cells are located. The compounds described herein are very potent at treating these cancers.

In certain circumstances, the compounds described herein can be employed as part of a pharmaceutical composition with other compounds intended to prevent or treat a particular cancer, i.e., combination therapy. In addition to effective amounts of the compounds described herein, the pharmaceutical compositions can also include various other components as additives or adjuncts.

Complexation with Proteins

The fulvene and fulvalene analogues described herein can be complexed with peptides and proteins, including albumin, transferrin, VEGF, bFGF, and the like. These complexes are easy to make and tend to have lower toxicity than the un-complexed compounds.

Those of skill in the art can readily appreciate how to complex the compounds described herein with a protein or peptide. The complexes can be administered in any manner in which the un-complexed compounds can be administered.

Combination Therapy

The combination therapy may be administered as (a) a single pharmaceutical composition which comprises a fulvene and/or fulvalene analogue as described herein, at least one additional pharmaceutical agent described herein, and a pharmaceutically acceptable excipient, diluent, or carrier; or (b) two separate pharmaceutical compositions comprising (i)

a first composition comprising a fulvene and/or fulvalene analogue as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, the fulvene and/or fulvalene analogues described herein can be administered together with at least one other chemotherapeutic agent as part of a unitary pharmaceutical composition. Alternatively, the fulvene and/or fulvalene analogues can be administered apart from the other anticancer chemotherapeutic agent. In this embodiment, the fulvene and/or fulvalene analogues and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering a fulvene and/or fulvalene analogue, as described herein, or a pharmaceutically acceptable salt or prodrug of a compound described herein, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosphamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anticancer compounds that can be used in combination with the fulvene and/or fulvalene analogues are described below.

The fulvene and/or fulvalene analogues can be combined with alpha-1-adrenoceptor antagonists, such as doxazosin, terazosin, and tamsulosin, which can inhibit the growth of prostate cancer cell via induction of apoptosis (Kyprianou, N., et al., Cancer Res 60:4550 4555, (2000)).

Sigma-2 receptors are expressed in high densities in a variety of tumor cell types (Vilner, B. J., et al., Cancer Res. 55: 408 413 (1995)) and sigma-2 receptor agonists, such as CB-64D, CB-184 and haloperidol, activate a novel apoptotic pathway and potentiate antineoplastic drugs in breast tumor cell lines. (Kyprianou, N., et al., Cancer Res. 62:313 322 (2002)). Accordingly, the fulvene and/or fulvalene analogues can be combined with at least one known sigma-2 receptor agonists, or a pharmaceutically acceptable salt of said agent.

The fulvene and/or fulvalene analogues can be combined with lovastatin, a HMG-CoA reductase inhibitor, and butyrate, an inducer of apoptosis in the Lewis lung carcinoma model in mice, can potentiate antitumor effects (Giermasz, A., et al., Int. J. Cancer 97:746 750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225 232 (2002)). Accordingly (in addition to forming fulvene and/or fulvalene analogues of these compounds), the fulvene and/or fulvalene analogues can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145 150 (1999)). 4HPR also was reported to have good activity in combination with gamma-radiation on bladder cancer cell lines (Zou, C., et al., Int. J. Oncol. 13:1037 1041 (1998)). Representative retinoids and synthetic retinoids include, but are not limited to, bexarotene, tretinoin, 13-cis-retinoic acid, 9-cis-retinoic acid, .alpha.-difluoromethylornithine, ILX23-7553, fenretinide, and N-4-carboxyphenyl retinamide.

Proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433 443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472 1478 (2002)). Representative tyrosine kinase inhibitors include, but are not limited to, Gleevec®, ZD1839 (Iressa®), SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544 3550 (2001)). Synergy of the protein farnesyltransferase inhibitor SCH66336 and cisplatin in human cancer cell lines also has been reported (Adjei, A. A., et al., Clin. Cancer Res. 7:1438 1445 (2001)). Prenyl-protein transferase inhibitors, including farnesyl protein transferase inhibitor, inhibitors of geranylgeranyl-protein transferase type I (GGPTase-I) and geranylgeranyl-protein transferase type-II, or a pharmaceutically acceptable salt of said agent, can be used in combination with the fulvene and/or fulvalene analogues described herein. Examples of known prenylprotein transferase inhibitors include, but are not limited to, R115777, SCH66336, L-778,123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209 4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Hunting) 16(No. 4 Suppl. 3):17 21 (2002)). Representative COX-2 inhibitors include, but are not limited to, celecoxib, valecoxib, and rofecoxib.

Any of the above-mentioned compounds can be used in combination therapy with the fulvene and/or fulvalene analogues. Additionally, many of these compounds can be converted to fulvene and/or fulvalene analogues by reaction of ketone, aldehyde, hydroxyl, thiol, and/or amine functional groups on the compounds using the chemistry described herein. The fulvene and/or fulvalene analogues of these compounds are within the scope of this invention.

Further, the fulvene and/or fulvalene analogues can be targeted to a tumor site by conjugation with therapeutically useful antibodies, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates can also enhance the anticancer effect of therapeutically useful antibodies, such as Herceptin® or Rituxan®.

The compounds can also be used in conjunction with surgical tumor removal, by administering the compounds before and/or after surgery, and in conjunction with radiation therapy, by administering the compounds before, during, and/or after radiation therapy.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the fulvene and/or fulvalene analogue is an amount sufficient to suppress the growth of the tumor(s), and, ideally, is a sufficient amount to shrink the tumor, and, more ideally, to destroy the tumor. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 µg/24 hr/patient. The effective dose generally does not exceed about 500, often does not exceed about 400, and frequently does not exceed about 300 µg/24 hr/patient. In addition, administration of the effective dose is such that the concentration of the compound within the plasma of the patient normally does not exceed 500 ng/mL and frequently does not exceed 100 ng/mL.

IV. Methods of Using the Compounds and/or Pharmaceutical Compositions

The compounds described herein, and pharmaceutical compositions including the compounds, can be used to treat cancers. Representative disorders that can be treated include neoplasms, such as hemangiomas, and malignant tumors, for example, those which arise in the setting of autocrine loops involving vascular endothelial growth factor (VEGF) and its major mitogenic receptor vascular endothelial growth factor receptor 2.

The cancers include those in which one of the Nox enzymes is present in elevated concentrations (i.e., Nox 1, Nox 4, and the like), or those in which cancer growth is mediated by ROS.

Representative malignant tumors include malignant endothelial tumors such as melanoma. Additional cancers that can be treated include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease, and malignant forms of these cancers.

In one embodiment, the cancer is melanoma, rectal carcinoma, colon carcinoma, breast carcinoma, ovarian carcinoma, small cell lung carcinoma, colon carcinoma, chronic lymphocytic carcinoma, hairy cell leukemia, esophogeal carcinoma, prostate carcinoma, breast cancer, myeloma, or lymphoma. It is believed that these cancers have circulating levels of tNOX (which may include Nox4 or other Nox enzymes) present in the sera of patients suffering from the cancer (see, for example, U.S. Pat. No. 5,605,810, which is hereby incorporated by reference in its entirety).

In some embodiments, the patient already has cancer and is undergoing treatment for the cancer, and may or may not have tumor metastasis (i.e., secondary cancer).

The cancer may be manifested in the form of a tumor, such as a tumor of epithelial tissue, lymphoid tissue, connective tissue, bone, or central nervous system.

The compounds can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Treatment of Osteoporosis

The compounds described herein can also be used to treat osteoporosis. The cytokine RANKL (receptor activator of NF-κB ligand) causes osteoporosis by activating osteoclasts. The compounds inhibit RANKL activity by potentiating apoptosis, suppresses osteoclastogenesis, and inhibits invasion through modulation of nuclear factor-kappaB activation pathway (see, for example, *Mol Cancer Res.* 2006 September; 4(9):621-33).

Treatment of Inflammatory Disorders

The compounds described herein are useful for treating or preventing inflammatory disorders. Reactive oxygen drives NFkB in inflammatory disorders such as rheumatoid arthritis, asthma, psoriasis, excema, lupus, scleroderma, certain heart diseases such atherosclerosis and coronary artery disease, and the like. Because the compounds are effective at inhibiting production of reactive oxygen species, they are active against inflammatory disorders.

The compounds also inhibit certain inflammatory signals, and can alleviate inflammatory disorders such as inflammatory arthritis by inhibiting these signals.

Rheumatoid arthritis (RA) is considered the most common systemic autoimmune disease, but other disorders, such as hypothyroidism, systemic lupus erythematosus (SLE), and the like can also be treated using the compounds described herein. A number of conditions are associated with chronic inflammation and elevated levels of TNF-α and IL-6, including rheumatoid arthritis, heart disease, and cancer. Numerous gastrointestinal disorders are caused by inflammation, including, but not limited to, Chrohn's disease, irritable bowel syndrome, and inflammatory bowel syndrome, and these disorders can also be treated and/or prevented using the compounds described herein.

There is a suggested link between rheumatoid arthritis and chronic inflammation due to the re-activation of Epstein-Barr virus (EBV), which latently infects a proportion of memory B cells in >90% of the world's population. Among the EBV-encoded proteins implicated in viral pathogenesis, considerable attention has focused upon latent membrane protein 1 (LMP1). Of the nine EBV genes expressed as proteins in EBV-transformed cells, LMP1 is the best characterized, and is the only EBV-encoded gene product capable of transforming cells in vitro and in vivo, resulting in the potential for lymphoproliferative changes and malignancy. In addition to its established role in the pathogenesis of B cell lymphoma and other malignancies, EBV infection may be linked to exacerbation of various human autoimmune diseases, including RA and SLE.

The mouse collagen-induced arthritis (CIA) model (Myers, et al., *Life Science* 61: 1861-1878 (1997)) has many pathologic and immunologic parallels to rheumatoid arthritis, and provides a stable, predictable model for evaluating the therapeutic potential of compounds for treating chronic inflammatory conditions. This model can be used, for example, to evaluate the ability of the compounds described herein to treat and/or prevent these disorders.

Treatment of mouse B cell lines with compounds described herein in vitro can be shown to recapitulate the cytokine profile seen in primary mouse B cells with a concomitant dose-dependent decrease in CD40 and LMP1-mediated NFkB and AP-1 activation. Those compounds which decrease CD40 and LMP1-mediated NFkB and AP-1 activation in a dose-dependent manner will be expected to have anti-inflammatory properties, potentially in both the cognitive phase of the immune response, as well as the effector phase, by inhibiting cytokines that lead to chronic inflammation and additional pathology.

Treatment of Ocular Disorders

The compounds are also suitable for use in treating ocular disorders with an inflammatory component, such as wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye.

Current methods for ocular delivery include topical administration (eye drops or other suitable topical formulations for direct administration to the eye), subconjunctival injections, periocular injections, intravitreal injections, surgical implants, and systemic routes.

Particularly where systemic toxicity is of concern when the oral and intravenous routes of administration are used, intravitreal injections, periocular injections, and sustained-release implants can be used to achieve therapeutic levels of drugs in ocular tissues. Eye drops are useful in treating conditions affecting either the exterior surface of the eye or tissues in the front of the eye, and some formulations can penetrate to the back of the eye for treatment of retinal diseases.

Certain disorders affect tissues at the back of the eye, where treatment is difficult to deliver. In these embodiments, iontophoresis can be used to deliver the compounds described herein to the back of the eye. For example, the ocular iontophoresis system, OcuPhor™, can deliver drugs safely and noninvasively to the back of the eye (Iomed). Iontophoresis uses a small electrical current to transportionized drugs into and through body tissues. Care must be taken not to use too high of a current density, which can damage eye tissues.

Iontophoresis typically involves using a drug applicator, a dispersive electrode, and an electronic iontophoresis dose controller. The drug applicator can be a small silicone shell that contains a conductive element, such as silver-silver chloride. A hydrogel pad can absorb the drug formulation. A small, flexible wire can connect the conductive element to the dose controller. The drug pad can be hydrated with a drug solution immediately before use, with the applicator is placed on the sclera of the eye under the lower eyelid. The eyelid holds the applicator in place during treatment. The drug dose and rate of administration can be controlled by programming and setting the electronic controller.

Treatment of Neurodegenerative Disorders and/or Providing Neuroprotection

Reactive oxygen species also induce inflammation and neurodegeneration. Inhibition of these species can also result in neuroprotection, including protection from further damage following an ischemic brain injury such as a stroke, or that caused from blunt trauma, and treatment or prevention of neurodegenerative disorders such as retinal degenerations, Alzheimer's disease, senile dementia, pre-senile dementia, Parkinsons disease, Huntington's Chorea, multiple sclerosis, and the like.

Reactive oxygen species also drive seizures, and the compounds described herein have GABAergic activity which may ameliorate seizures as well.

Treatment of Vascular Disorders

Vascular diseases such as erectile dysfunction and migraines in which ROS have been implicated may also respond to NADPH oxidase inhibitors.

In all of these treatments, the compounds are believed to function by inhibiting one or more Nox enzymes, such as Nox1-5, or by stimulating superoxide scavengers (and thus inhibiting ROS production), or directly reacting with and inactivating ROS.

Nox2-containing NADPH oxidase and Akt activation are believed to play a key role in angiotensin II-induced cardiomyocyte hypertrophy (Physiol. Genomics 26: 180-191, 2006) Inhibition of this Nox enzyme can therefore be used to treat or prevent angiotensin II-induced cardiomyocyte hypertrophy.

The following examples are provided to illustrate the present invention, and should not be construed as limiting thereof. In these examples, all parts and percentages are by weight, unless otherwise noted. Reaction yields are reported in mole percentages.

EXAMPLES

The following examples are provided to illustrate the present invention and should not be construed as limiting the scope thereof. In these examples, all parts and percentages are by weight, unless otherwise noted. Reaction yields are reported in mole percentage.

Example 1

Spectrophotometric Assay of NADH Oxidase

NADH oxidase activity can be determined as the disappearance of NADH measured at 340 nm in a reaction mixture containing 25 mM Tris-Mes buffer (pH 7.2), 1 mM KCN, and 150 µM NADH at 37° C. Activity can be measured, for example, using a Hitachi U3210 spectrophotometer with stirring and continuous recording over two intervals of 5 min each. A millimolar extinction coefficient of 6.22 can be used to determine specific activity.

Example 2

Measuring Cell Growth

A mouse mammary tumor subpopulation line 4T1 arising from a BALB/cf C3H mouse can be grown in DME-10, Dulbecco's modified Eagle's medium supplemented with 5% fetal calf serum, 5% newborn calf serum, 1 mM mixed nonessential amino acids, 2 mM L-glutamine, penicillin (100 units/ml), and streptomycin (100 µg/ml) (Miller et al., 1987, Brit. J. Can. 56:561-569 and Miller et al., 1990, Invasion Metastasis 10:101-112).

Example 3

Inhibition of Nox2 Enzyme by Various Test Compounds

Various test compounds were examined for activity against Nox2 enzyme by determining hydrogen peroxide ($H_2O_2$) production in phorbol 12-myristate 13-acetate (PMA)-stimulated Cos-phox cells treated with different concentrations of vehicle control or a test compound listed in Table 1.

TABLE 1

| Test Compounds | |
|---|---|
| No. | Name |
| 1 | BWL-63-11 |
| 2 | BWL-90-3C |
| 3 | BWL-304-1 |
| 4 | BWL-115-7 |
| 5 | BWL-325-3F |
| 6 | BWL-42-2 |
| 7 | cyclopentadiene hydrazine |
| 8 | 6-dimethylamino fulvene |
| 9 | BWL-42-2 |
| 10 | Indigo fulvene |
| 11 | Dihydroxy-tert-butyl-fulvene |
| 12 | Phosphorous-oxy-fulvene |
| 13 | Carbazole blue |
| 14 | Ethylcarbazole blue |
| 15 | Impramine blue |
| 16 | Curcumin fulvene |
| 17 | Ninhydrine fulvene |
| 18 | Dodecane fulvene |

Cos-phox cells have been described previously in Price et al., Blood, 99: 2653-61 (2002), which is incorporated herein by reference.

$H_2O_2$ release was measured using the homovanillic acid assay as described previously in Martyn et al., *Cellular Signalling*, 18:69-82 (2006) and Perry et al., *J. Invest. Dermatol.*, 126:2316-22 (2006), which are incorporated herein by reference. Briefly, $1.5$-$1.75 \times 10^5$ cells/well of a 12-well plate were seeded with Cos-phox cells. The following day, cells were washed once with Hank's balanced salt solution, stimulated with 0.4 mg/ml phorbol 12-myristate 13-acetate (PMA), and then preincubated for 15 minutes with either vehicle control or different concentrations (i.e., 1 µM, 5 µM, or 20 µM) of test compound no. 8, 10, 15, 16, 17, or 18 in 1 ml of media. The cells were then washed once with Hank's balanced salt solution. Vehicle control or different concentrations of test compound no. 8, 10, 15, 16, 17, or 18 were added at the same concentrations as in pretreatment to 0.5 ml of homovanillic acid assay solution (100 mM homovanillic acid assay, 4 U/ml horseradish peroxidase in Hank's balanced salt solution with $Ca^{2+}$ and $Mg^{2+}$) and incubated with the cells for 1 hour at 37° C. The reaction was stopped by adding 75 ml of homovanillic acid assay stop buffer (0.1 M glycine/0.1 M NaOH (pH 12) and 25 mM EDTA in phosphatebuffered saline). Fluorescence was read on a BioTek Synergy HT (BioTek Instruments Inc., Winooski, Vt., CA) with an excitation of 320 nm and emission of 440 nm.

Cox-phox cells did not produce $H_2O_2$ without PMA stimulation with (data not shown) or without the addition of the test compounds, therefore, in this particular system, detection of Nox2 activity required PMA. The ability of test compound no. 8, 10, 15, 16, 17, or 18 to inhibit production of $H_2O_2$ in Cox-phox cells is shown in FIG. 1 as a percentage relative to the untreated control (100%).

The results showed that test compound nos. 8, 10, 15, 16, 17, and 18 inhibited Nox2 enzyme in a dose-dependent manner.

Example 4

In Vitro Testing of Various Test Compounds

Nude mice were injected subcutaneously with approximately one million tumor cells. Once tumors became visible, they were treated with 40 mg/kg daily of circumin fulvene. The compound was reconstituted in 100 microliters of ethanol and diluted with 900 microliters of 20% Intralipid, and 0.3 ml of this mixture was injected intraperitoneally daily. Tumors were measured with vernier calipers, and tumor volume was calculated using the formula (width$^2 \times$length) 0.52, where width is the smallest dimension, 2 represents squared, and 1 represents the length.

Figure 2:
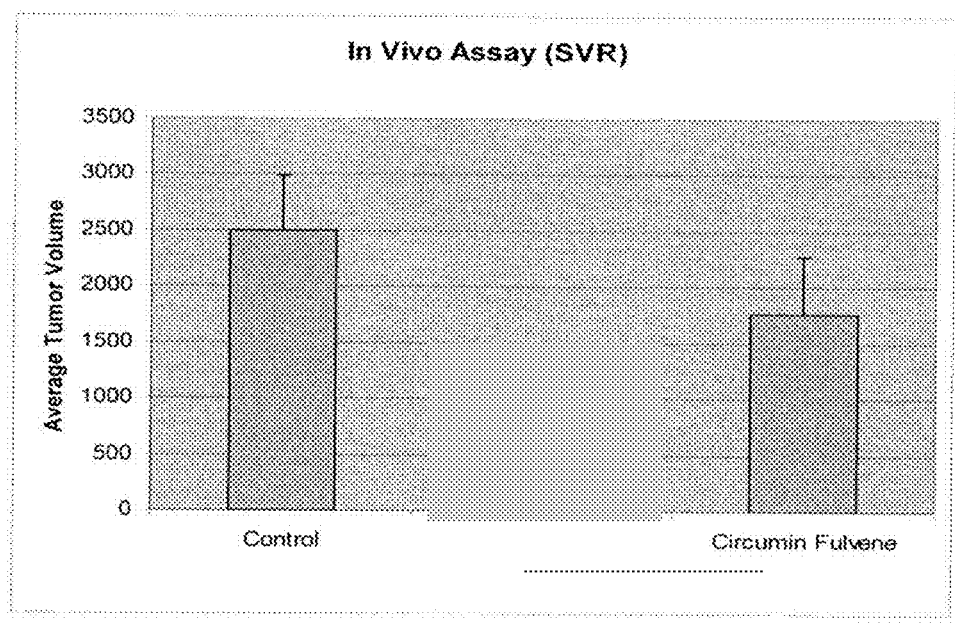
FIG. 2 is a chart showing the effect of curcumin fulvene against tumor cells in vivo (average tumor volume).

The results are shown in Table 1, below, and in FIG. 2.

TABLE 1

Treatment with Curcumin Fulvene

| Group | L | W | Tumor Volume | Average | Control | Circumin Fulvene |
|---|---|---|---|---|---|---|
| Control | 12.42 | 10.18 | 669.2994922 | | | |
| | 21.82 | 21.24 | 5118.787665 | | | |
| | 22.58 | 11.98 | 1685.159129 | 2491.082 | 2491.082 | 1767.914 |
| Curcumin Fulvene | 14.52 | 12.09 | 1103.627622 | | | |
| | 13.76 | 8.89 | 565.4904819 | | | |
| | 25.83 | 16.45 | 3634.624539 | 1767.914 | | |

Example 5

The NADPH Oxidase Inhibitor Fulvene-5 Diminishes Light-Induced Retinal Function Loss in Albino Mice Exposing albino mice to bright light causes loss of retinal function, an effect partially mediated by damage caused by reactive oxygen species (ROS). Activation of NADPH oxidase by various stressors increases ROS production. The purpose of these experiments was to test whether light-induced retinal function loss is mediated by NADPH oxidase activity.

Methods:

Balb-C mice were exposed to dim (20 lux) or bright (10,000 lux) white light for 6 hours. Mice were injected with Fulvene-5, a triphenylmethane that inhibits NADPH oxidase, dissolved in vehicle (intralipid-DMSO) or vehicle alone. Intraperitoneal injections were given daily for two weeks. Electroretinograms (ERGs) were taken 0, 7, and 14 days following light exposure.

Figure 3:
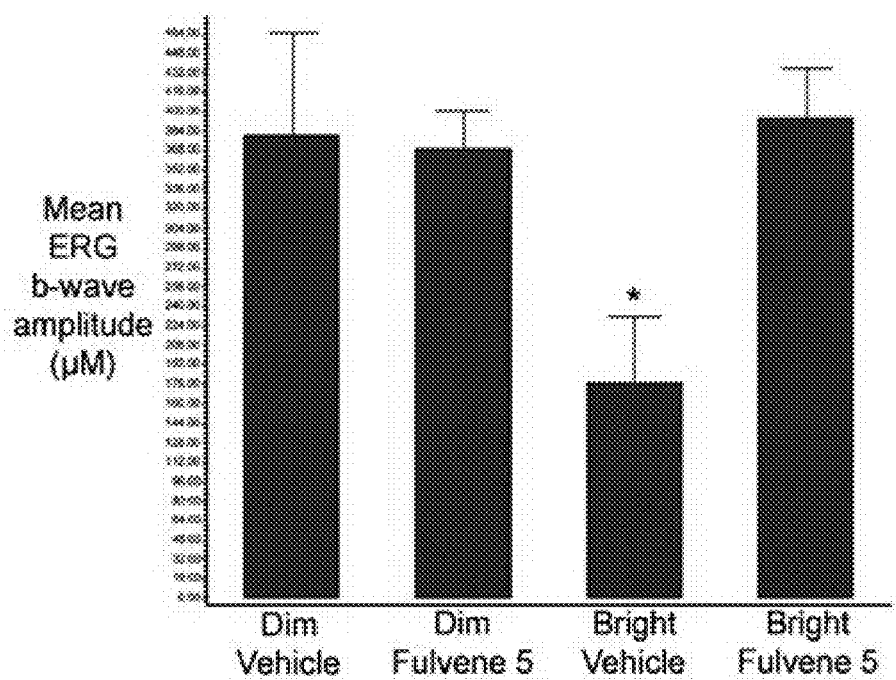
FIG. 3 is a chart showing the mean ERG b-wave amplitude (μm) for mice treated with either vehicle or Fulvene-5 (4-(cyclopenta-2,4-dienylidine methyl)-5-methyl-1H-imidazole), and exposed to either dim light or bright light.

Results:

Mice injected with vehicle and exposed to bright light exhibited significantly diminished ERG a-wave and b-wave amplitudes compared to mice exposed to bright light but treated with Fulvene-5 or compared to mice exposed to dim light. The results are shown in FIG. 3.

Conclusions:

Treatment with the NADPH oxidase inhibitor Fulvene-5 precluded the damaging effects of bright light exposure on retinal function as measured by ERG. It may be that bright light exposure results in activation of NADPH oxidase resulting in increased ROS production causing retinal cell damage. Retinal morphology, apoptosis, NADPH oxidase enzyme activity, redox status, and ROS content are currently being analyzed.

Mice were exposed to either dim light (control) or bright light of an intensity that causes retinal degeneration (Light Induced Retinal Degeneration; LIRD). This is a classic rodent model of retinal degeneration. For each lighting condition, half the animals were injected with vehicle and the other half were injected with Fulvene 5. Electroretinograms (ERGs) of the treated mice were measured at one week post-exposure. An ERG is a measure of the change in electrical potential across the eyeball in response to a flash of light, and is used as an indication of retinal function.

The data showed that bright light exposure induced about a 50% suppression of ERG b-wave amplitude at one week. However, rats injected daily with Fulvene 5 showed no suppression of ERG amplitude, suggesting that Fulvene 5 prevented visual function loss at one week. The data is summarized in FIG. 3.

Example 6

ESR Spectrum of a Representative Fulvene and Superoxide Dismutase

Li used ESR to confirm the production of NADPH-dependent $.O_2-$ by isolated endosomes (Li et al., *Molecular and Cellular Biology*, January 2006, p. 140-154, 26(1):140-154 (2006)). ESR assays were conducted at room temperature using a Bruker model EMX ESR spectrometer (Bruker). Vesicular fractions from each sample were mixed with the spin trap, 50 mM 5,5-dimethyl-1-pyrroline N-oxide (DMPO), in a total volume of 500 µl of PBS, pH 7.4. This solution contained iminodiacetic acid-chelating resin (10 ml/liter; Sigma-Aldrich). The reaction was initiated by adding NADPH to 100 µM and was immediately placed into the ESR spectrometer. DMPO-hydroxyl radical adduct formation was assayed for 10 min. Instrument settings were as follows: receiver gain, $1 \times 10^6$; modulation frequency, 100 kHz; microwave power, 40.14 mW; modulation amplitude, 1.0 G; and sweep rate, 1 G/s.

Figure 4:
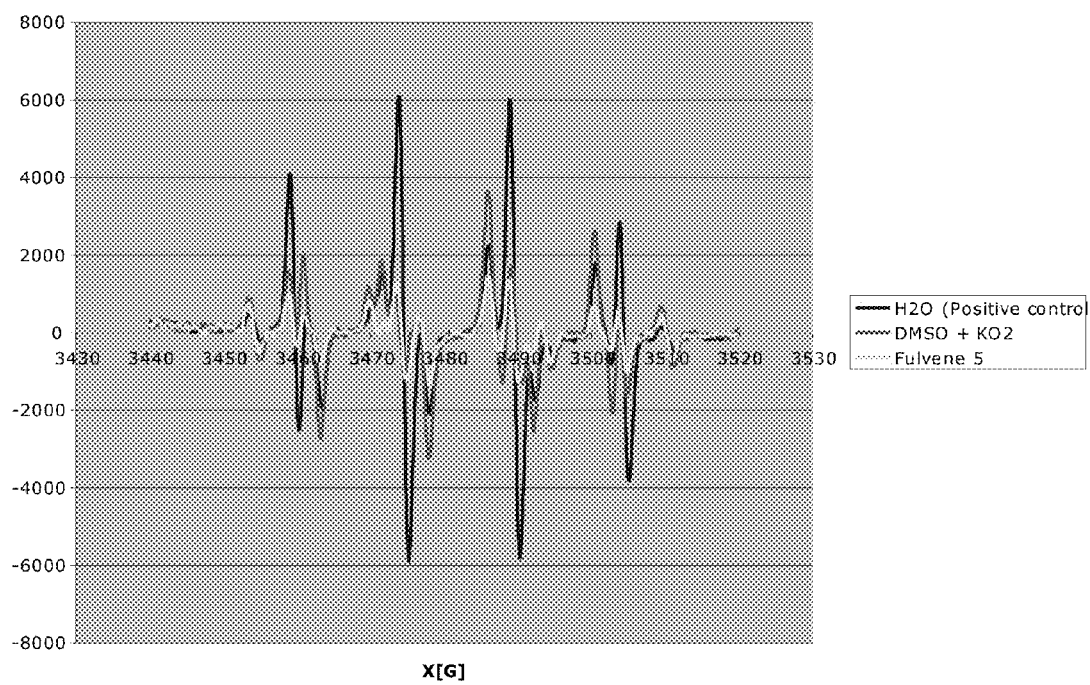
FIG. 4 is an electron spin resonance ("ESR") spectra of superoxide dismutase and Fulvene 5 ("Indigo fulvene").

In the instant application, the ESR spectrum of Fulvene 5 and of superoxide dismutase were taken using conditions substantially as described in Li et al. The ESR spectra (FIG. 4) shows that Fulvene 5 appears to form a radical by reacting with superoxide, thus inhibiting the ability of superoxide dismutase to generate ROS.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention claimed is:

1. A compound of the following formula:

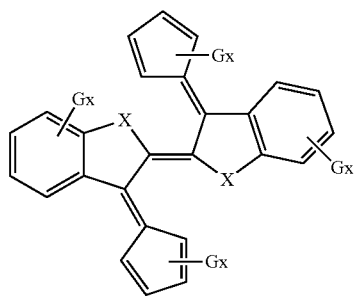

or salts thereof wherein
X is O, S, CH$_2$, or NR',
x and y are integers between 0 and 3; and
G is C$_{1-6}$alkyl, cycloalkyl, alkenyl, heterocyclyl, aryl, heteroaryl, halo, —OR', —NR'R", —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", and —NR'SO$_2$R", where
R' and R" are individually hydrogen, C$_{1-6}$alkyl, cycloalkyl, heterocyclyl, aryl, arylalkyl or benzyl.

2. A compound of formula I having the following formula:

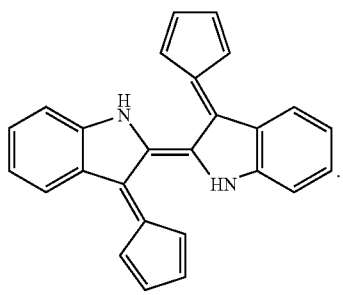 [SMILES: C1=CC(=c2/c(=c3\[nH]c4ccccc4c3=C3C=CC=C3)[nH]c3ccccc23)C=C1]

3. A pharmaceutical composition comprising a compound of claim 1 or pharmaceutically acceptable salt thereof.